US009192509B2

(12) United States Patent
Muehlbauer et al.

(10) Patent No.: US 9,192,509 B2
(45) Date of Patent: Nov. 24, 2015

(54) METHODS AND APPARATUS FOR THERAPEUTIC APPLICATION OF THERMAL ENERGY INCLUDING BLOOD VISCOSITY ADJUSTMENT

(71) Applicants: Thomas G. Muehlbauer, San Diego, CA (US); Jeffrey R. Gray, San Diego, CA (US)

(72) Inventors: Thomas G. Muehlbauer, San Diego, CA (US); Jeffrey R. Gray, San Diego, CA (US)

(73) Assignee: AVACEN, INC., San Diego, CA (US)

( * ) Notice: Subject to any disclaimer, the term of this patent is extended or adjusted under 35 U.S.C. 154(b) by 0 days.

(21) Appl. No.: 13/794,413

(22) Filed: Mar. 11, 2013

(65) Prior Publication Data

US 2014/0257440 A1    Sep. 11, 2014

(51) Int. Cl.
*A61F 7/00* (2006.01)
*A61F 7/02* (2006.01)
*A61B 19/00* (2006.01)

(52) U.S. Cl.
CPC . *A61F 7/00* (2013.01); *A61F 7/007* (2013.01); *A61F 7/0053* (2013.01); *A61B 2019/465* (2013.01); *A61F 2007/0036* (2013.01); *A61F 2007/0075* (2013.01); *A61F 2007/0086* (2013.01); *A61F 2007/0091* (2013.01); *A61F 2007/0093* (2013.01); *A61F 2007/0239* (2013.01)

(58) Field of Classification Search
USPC .............. 607/96, 111, 112, 108, 106; 601/18
See application file for complete search history.

(56) References Cited

U.S. PATENT DOCUMENTS

| | | | |
|---|---|---|---|
| 1,399,095 A | | 12/1921 | Webb, Sr. |
| 1,740,624 A | | 12/1929 | Peel |
| 2,235,138 A | * | 3/1941 | Billetter ............................ 601/9 |
| 3,859,989 A | * | 1/1975 | Spielberg ........................ 601/11 |
| 4,329,997 A | | 5/1982 | De Yampert et al. |
| 4,735,195 A | | 4/1988 | Blum et al. |

(Continued)

FOREIGN PATENT DOCUMENTS

| | | |
|---|---|---|
| WO | WO-98/40039 | 9/1998 |
| WO | WO-03/007804 A2 | 1/2003 |

(Continued)

OTHER PUBLICATIONS

Machine Translation of WO 2004046551; Inventors Ise and Ohtani; published Jun. 3, 2004.*

(Continued)

*Primary Examiner* — Kaitlyn Smith
(74) *Attorney, Agent, or Firm* — Foley & Lardner LLP; Christopher C. Bolten; Nicola A. Pisano

(57) ABSTRACT

Apparatus and methods are provided for treating a human condition by providing an appendage chamber having a thermal exchange member. Negative pressure may be applied to a human appendage when placed within the appendage chamber. Blood flowing through the arteriovenous anastomosis (AVA) of the appendage may be heated or cooled at the thermal exchange member for therapeutic application of thermal energy to adjust blood viscosity in the human to alleviate symptoms associated with a number of autoimmune, circulatory, neurological, lymphatic, and endocrinal maladies. A load sensor may be coupled to the thermal exchange member and configured to measure a force of the appendage applied to the thermal exchange member. In addition, a negative pressure sensor may measure pressure within the appendage chamber.

9 Claims, 11 Drawing Sheets

(56) References Cited

U.S. PATENT DOCUMENTS

| | | |
|---|---|---|
| 5,027,795 A | 7/1991 | Kato |
| 5,369,807 A | 12/1994 | Cho et al. |
| 5,425,742 A * | 6/1995 | Joy .................... 606/203 |
| 5,637,076 A | 6/1997 | Hazard et al. |
| 5,683,438 A | 11/1997 | Grahn |
| 5,688,208 A | 11/1997 | Plemmons |
| 5,693,004 A | 12/1997 | Carlson et al. |
| 5,733,318 A | 3/1998 | Augustine |
| 6,149,674 A | 11/2000 | Borders |
| 6,315,696 B1 | 11/2001 | Garrioch |
| 6,434,423 B1 | 8/2002 | Ross |
| 6,602,277 B2 | 8/2003 | Grahn et al. |
| 6,656,208 B2 | 12/2003 | Grahn et al. |
| 6,673,099 B2 | 1/2004 | Grahn et al. |
| 6,752,794 B2 | 6/2004 | Lockwood et al. |
| 6,846,322 B2 | 1/2005 | Kane et al. |
| 6,966,922 B2 | 11/2005 | Grahn et al. |
| 6,974,442 B2 | 12/2005 | Grahn et al. |
| 7,122,047 B2 | 10/2006 | Grahn et al. |
| 7,160,316 B2 | 1/2007 | Hamilton et al. |
| 7,169,119 B2 | 1/2007 | Chan et al. |
| 7,182,776 B2 | 2/2007 | Grahn et al. |
| 7,862,600 B2 | 1/2011 | Grahn et al. |
| 7,972,287 B2 * | 7/2011 | Stewart et al. ............... 601/7 |
| 8,460,355 B2 * | 6/2013 | Cazzini et al. ............. 607/111 |
| 8,569,566 B2 * | 10/2013 | Blott et al. ................. 602/41 |
| 8,603,150 B2 * | 12/2013 | Kane et al. ................ 607/111 |
| 2001/0049546 A1 | 12/2001 | Dvoretzky et al. |
| 2002/0151826 A1 * | 10/2002 | Ramey et al. ................ 601/6 |
| 2003/0004083 A1 | 1/2003 | France |
| 2003/0040783 A1 | 2/2003 | Salmon |
| 2004/0015127 A1 * | 1/2004 | Silver et al. ................ 604/74 |
| 2005/0051174 A1 * | 3/2005 | Emerson ................ 128/207.14 |
| 2006/0111766 A1 | 5/2006 | Grahn et al. |
| 2007/0060987 A1 | 3/2007 | Grahn et al. |
| 2007/0088250 A1 * | 4/2007 | Silver et al. ................ 604/74 |
| 2007/0093730 A1 | 4/2007 | Chan et al. |
| 2007/0112400 A1 | 5/2007 | Hamilton et al. |
| 2007/0123962 A1 | 5/2007 | Grahn et al. |
| 2007/0240247 A1 | 10/2007 | Beck |
| 2008/0004549 A1 * | 1/2008 | Anderson et al. ............. 601/6 |
| 2008/0021531 A1 | 1/2008 | Kane et al. |
| 2008/0034466 A1 | 2/2008 | Zicarelli |
| 2008/0077201 A1 | 3/2008 | Levinson et al. |
| 2008/0077205 A1 | 3/2008 | Cazzini |
| 2008/0132816 A1 | 6/2008 | Kane et al. |
| 2008/0132976 A1 * | 6/2008 | Kane et al. ................. 607/104 |
| 2008/0208088 A1 | 8/2008 | Cazzini et al. |
| 2008/0249593 A1 * | 10/2008 | Cazzini et al. ............. 607/111 |
| 2008/0300515 A1 | 12/2008 | Nozzarella et al. |
| 2009/0036959 A1 * | 2/2009 | Filtvedt et al. ............. 607/104 |
| 2009/0048649 A1 | 2/2009 | Peret et al. |
| 2009/0112298 A1 | 4/2009 | Jusiak et al. |
| 2009/0177184 A1 | 7/2009 | Christensen et al. |
| 2009/0240191 A1 * | 9/2009 | Loori et al. .................. 604/23 |
| 2010/0106199 A1 * | 4/2010 | Sawa et al. ................. 606/304 |
| 2010/0106230 A1 * | 4/2010 | Buchanan et al. ........... 607/111 |
| 2010/0152633 A1 | 6/2010 | Rein et al. |
| 2010/0152821 A1 * | 6/2010 | Rein et al. ................... 607/96 |
| 2010/0262048 A1 | 10/2010 | Shinomiya et al. |
| 2010/0280448 A1 * | 11/2010 | Lantz et al. .................. 604/74 |
| 2011/0000484 A1 | 1/2011 | Melsheimer ............. 128/202.12 |
| 2011/0071465 A1 * | 3/2011 | Wang et al. .................. 604/67 |
| 2011/0092893 A1 * | 4/2011 | Demers et al. ............... 604/29 |
| 2011/0092894 A1 * | 4/2011 | McGill et al. ................ 604/29 |
| 2011/0098635 A1 * | 4/2011 | Helmore et al. .............. 604/29 |
| 2011/0106002 A1 * | 5/2011 | Helmore et al. .............. 604/29 |
| 2011/0125085 A1 * | 5/2011 | McGill et al. ................ 604/29 |
| 2011/0172749 A1 | 7/2011 | Christensen et al. |
| 2012/0095420 A1 * | 4/2012 | Anderson et al. ............ 604/319 |
| 2012/0123322 A1 * | 5/2012 | Scarpaci et al. .............. 604/29 |
| 2012/0191022 A1 * | 7/2012 | Muehlbauer et al. ........... 601/18 |
| 2013/0165847 A1 * | 6/2013 | Scarpaci et al. .............. 604/28 |
| 2013/0184638 A1 * | 7/2013 | Scarpaci et al. .............. 604/28 |

FOREIGN PATENT DOCUMENTS

| | | | |
|---|---|---|---|
| WO | WO 2004046551 A1 * | 6/2004 | ............. F04B 39/12 |
| WO | WO-2005/030101 A1 | 4/2005 | |
| WO | WO-2012/012683 A1 | 1/2012 | |
| WO | WO 2012012683 A1 * | 1/2012 | ............... A61F 7/00 |
| WO | WO2012012683 A1 * | 1/2012 | ............... A61F 7/00 |

OTHER PUBLICATIONS

Grahn et al., Recovery from mild hypothermia can be accelerated by mechanically destending blood vessels in the hand, J. Appl. Physiol., 85(5):1643-1648 (1998).

PCT International Search Report and Written Opinion dated Sep. 26, 2014 in PCT Patent Application No. PCT/US2014/021355.

* cited by examiner

METHODS AND APPARATUS FOR THERAPEUTIC APPLICATION OF THERMAL ENERGY INCLUDING BLOOD VISCOSITY ADJUSTMENT

I. FIELD OF THE INVENTION

This application generally relates to therapeutic manipulation of mammalian thermoregulation.

II. BACKGROUND OF THE INVENTION

The body temperature of mammals is normally tightly controlled by an autonomic regulatory system referred to herein as the thermoregulatory system. A primary effector of this regulatory system is blood flow to specialized skin areas where heat from the body core may be dissipated to the environment. Normally, when body and/or environmental temperatures are high, the dilation of certain blood vessels favors high blood flow to these skin areas, and as environmental and/or body temperatures fall, vasoconstriction reduces blood flow to these skin areas and minimizes heat loss to the environment.

Strategic inducement of vasodilation and heat transfer in targeted portions of the body, such as the extremities, may exert positive therapeutic benefits in remote regions of the body. For example, manipulating heat transfer across the skin may change the core temperature of the mammalian body in response. Unfortunately, it may be difficult to induce such changes to an extent sufficient for therapy, given the human body's refined ability to thermoregulate to maintain temperature homeostasis or normothermia.

By applying heat and subatmospheric (negative) pressure to a hypothermic individual's skin, normothermia may be achieved (see, e.g., Grahn et al., "Recovery from mild hypothermia can be accelerated by mechanically distending blood vessels in the hand," J. Appl Physiol. (1998) 85(5):1643-8). Other therapeutic applications for cooling the skin to achieve normothermia have also been described; e.g., in treating cancer as described in U.S. Pat. No. 7,182,776 to Grahn. However, therapeutic applications for continuously applying heat to the skin while at normothermia to increase microvascular circulation and/or to adjust blood viscosity have not been demonstrated.

Every year, millions of dollars are spent on treatments and drugs for reducing blood viscosity. Such drugs suffer from a variety of drawbacks including cost and side effects such as dizziness, headache, nausea, vomiting, chest pain, and irregular heartbeat.

In view of the foregoing drawbacks of previously known systems, it would be desirable to provide a robust and economical system to increase whole body circulation and to increase or decrease blood viscosity.

III. SUMMARY OF THE INVENTION

The present invention overcomes the drawbacks of previously-known apparatus by providing apparatus for treating a condition of a human that includes an appendage chamber, a thermal exchange member, and a pressure source. The appendage chamber may be configured to accept a human appendage, e.g., hand or foot, containing an arteriovenous anastomosis (AVA). The thermal exchange member is disposed within the appendage chamber and configured to selectively heat or cool blood flowing through the AVA. The pressure source is coupled to the appendage chamber and configured to apply negative pressure within the appendage chamber.

In accordance with one aspect of the present invention, the apparatus may include a load sensor coupled to the thermal exchange member and configured to measure a force of the appendage applied to the thermal exchange member. The load sensor may be electrically coupled to a programmable controller configured to: (a) determine a base force measured using the load sensor, (b) calculate and set a force range using the base force, (c) monitor whether the force of the appendage measured by the load sensor falls within the force range, (d) send an alert if the force is outside the force range, and (e) adjust the force range over time to accommodate ambient temperature variations caused by heating or cooling the thermal exchange member.

In accordance with another aspect of the present invention, the appendage chamber may include an expandable cuff with an appendage opening configured to accept the appendage. The pressure source may be coupled to the expandable cuff and configured to apply positive pressure to expand, e.g., inflate, the expandable cuff to seal around the appendage. The apparatus may include a flexible membrane having a membrane opening configured to accept the appendage such that the flexible membrane conforms to the expandable cuff as the pressure source applies positive pressure. The appendage chamber also may include a pressure chamber insert (PCI) having the expandable cuff, wherein the PCI is configured to be removable from the appendage chamber.

The apparatus may include a sealing pad disposed within the appendage chamber and having a sealing pad opening configured to be disposed around the thermal exchange member. The sealing pad is configured to be coupled to the PCI to enhance application of negative pressure within the PCI. The apparatus also may include a deformable pad disposed within the appendage chamber and configured to contact the appendage and the appendage chamber to urge the appendage onto the thermal exchange member.

In accordance with one aspect of the present invention, the pressure source is disposed within the appendage chamber, coupled to the expandable cuff, and configured to apply positive pressure to expand the expandable cuff to seal around the appendage and to apply negative pressure to the appendage when placed within the appendage chamber. The apparatus may include a negative pressure sensor configured to measure a pressure within the appendage chamber. The negative pressure sensor may be electrically coupled to a programmable controller configured to monitor the pressure measured by the negative pressure sensor and direct the pressure source to expand the expandable cuff if the measured pressure is above a predetermined pressure The thermal exchange member may include a Peltier device or electric heating device coupled to a metal or plastic pad and configured to heat or cool the thermal exchange member. The thermal exchange member also may include electrical heating components. The thermal exchange member may be configured to be heated to a suitable temperature, e.g., between 107-110° F. or between 100-120° F., or cooled to a suitable temperature, e.g., between 58-64° F. or between 58-95° F., or both. In one embodiment, the thermal exchange member is configured to heat or cool the blood at a temperature and for a duration sufficient to adjust the viscosity of blood in the human.

The programmable controller may be configured to control the application of negative pressure within the appendage chamber, e.g., within the PCI, and may be configured to monitor application of negative pressure within the appendage chamber responsive to the pressure measured by the negative pressure sensor. The programmable controller further is configured to control heating or cooling of the thermal exchange member responsive to user input or a preselected therapy regime. The preselected therapy regime may be selected to alleviate a symptom associated with an autoimmune, circulatory, neurological, lymphatic, thermoregulatory disorders, or endocrinal dysfunction, or any combination thereof including, but not limited to, Parkinson's disease, diabetic neuropathy, migraine headaches, Alzheimer's disease, fibromyalgia, Lyme disease, bipolar disorder, schizophrenia, attention deficit disorder (ADD), attention deficit hyperactivity disorder (ADHD), obsessive compulsive disorder (OCD), and Autism.

In accordance with another aspect of the present invention, a method for adjusting viscosity of blood is provided. The method may include providing an appendage chamber, a thermal exchange member disposed within the appendage chamber, and a pressure source coupled to the appendage chamber; disposing a human appendage containing an arteriovenous anastomosis (AVA) within the appendage chamber; applying negative pressure in the appendage chamber using the pressure source; and heating or cooling the thermal exchange member to deliver heating or cooling to blood flowing through the AVA at a temperature and for a duration sufficient to adjust the viscosity of the blood to alleviate a symptom associated with at least one of an autoimmune, circulatory, neurological, lymphatic, thermoregulatory, or endocrinal malady.

The heating or cooling may include heating or cooling the thermal exchange member to deliver heating or cooling for approximately five to thirty minutes.

In one embodiment, negative pressure is applied in the appendage chamber, and optionally in the PCI, using the pressure source and maintaining the negative pressure between −20 mmHg and −40 mmHg or between −1 mmHg and −50 mmHg.

The adjustment in viscosity of blood may increase microvascular circulation and alleviate a symptom associated with hypertension, occlusive arterial disease, myocardial infarction, kidney failure, liver failure, hyperglycemia, preeclampsia, dyslipidemia, and diseases or conditions associated with systemic inflammation or hyperviscosity of the blood.

IV. BRIEF DESCRIPTION OF THE DRAWINGS

V. DETAILED DESCRIPTION OF THE INVENTION

Figure 1A:
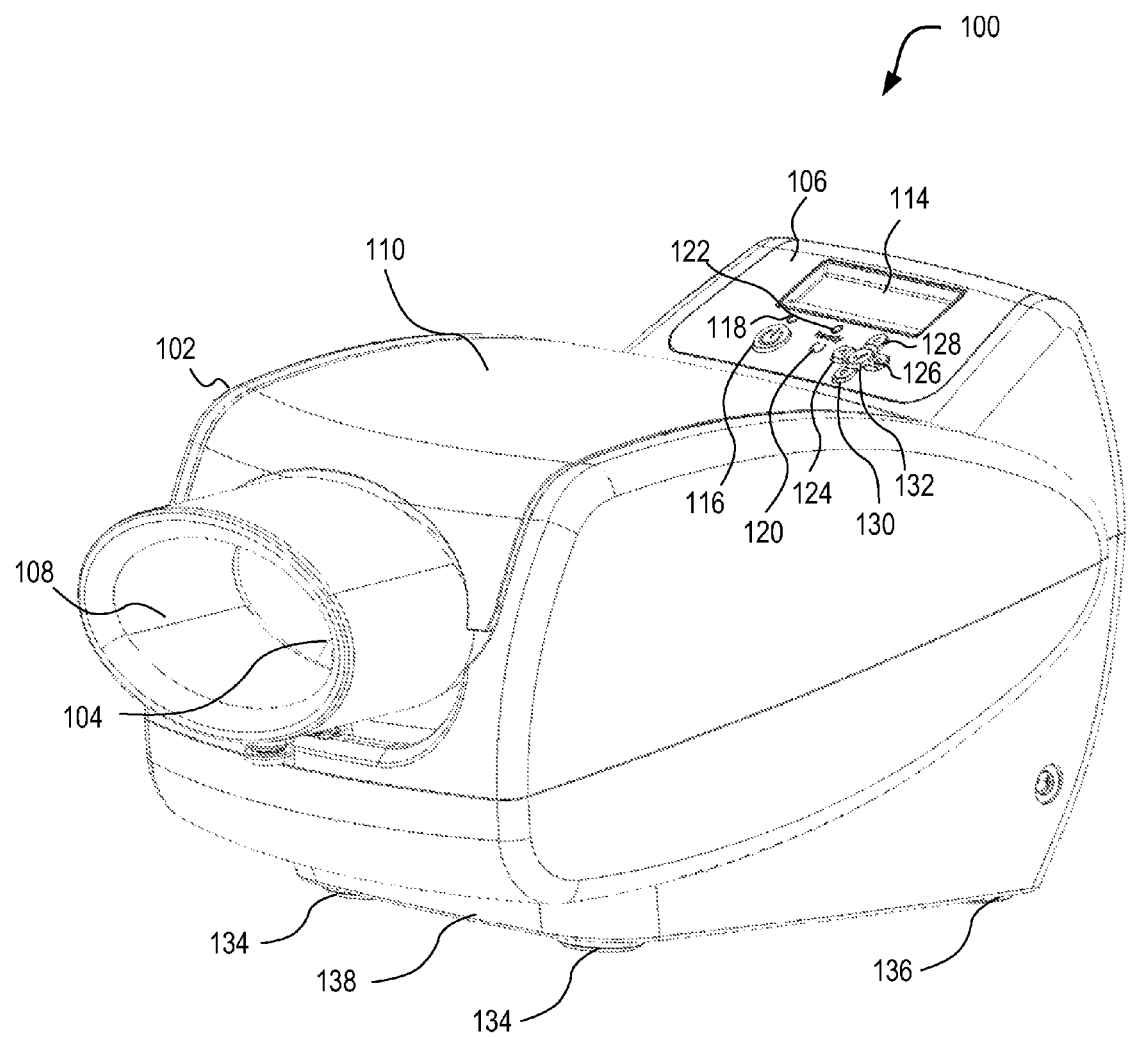
FIG. 1A is a perspective view of an exemplarily apparatus for treating a condition constructed in accordance with one aspect of the present invention.

The present invention provides methods and apparatus for applying thermal energy to a human to increase or rebalance blood circulation, and/or stimulate the lymphatic or endocrine systems to address a variety conditions. The methods and apparatus of the present invention are expected to provide beneficial results in treating a number of common ailments, including improved healing of acute and chronic wounds, and relief from neurological and hormone-relating ailments as described in U.S. Patent Application Publication No. 2012/0191022 to Muehlbauer, assigned to the assignee of the present invention, the entire contents of which are incorporated herein by reference.

In accordance with one aspect of the present invention, apparatus is provided that includes an appendage chamber, a pressure source, and a thermal exchange member. In one embodiment, the apparatus provides a negative pressure environment that assists in maintaining vasodilation and enhances the transfer to energy to an arteriovenous anastomosis (AVA) vascular area of the palm of a human hand. The AVA vascular area may experience vasodilation from pre-treatment hypernormothermia and/or heat delivered to the area from the thermal exchange member during treatment. This vasodilation increases the heat exchange between the thermal exchange member and the circulatory system by increasing blood flow within the palm AVA's. An appendage chamber, e.g., clam shell, glove-like, boot-like, or sleeve-like chamber, may be used to provide a negative pressure environment while providing heating or cooling to an appendage using a thermal exchange system for a preselected time, e.g., between approximately 5 and 30 minutes. While embodiments of the invention will be described further below with respect to a chamber configured to receive a hand, it is recognized that the appendage chamber may be adapted for use with other appendages containing an AVA suitable for the vasodilation methods described herein, such as vasculatures in the foot.

The present invention further provides methods and apparatus for applying thermal energy to a human to increase or decrease blood viscosity to address a variety of medical conditions such as autoimmune, circulatory, neurological, lymphatic, and endocrinal maladies.

Apparatus Overview

Referring to FIGS. 1A, 1B, 1C, and 1D, apparatus 100 for treating a condition is provided, including appendage chamber 102, thermal exchange member 104, and control panel 106. Appendage chamber 102 includes a housing configured to accept a human appendage containing an AVA such as a hand, for example, through appendage opening 108. In preferred embodiments, appendage chamber 102 comprises a durable and relatively rigid plastic or metal alloy, or combination thereof, of which individual components may be formed using conventional injection-molding or stamping processes. Appendage chamber 102 preferably includes pressure chamber insert (PCI) 110 that may be partially or fully transparent such that a user and/or physician may monitor the hand during treatment. Preferably, PCI 110 comprises a rigid, substantially transparent plastic or polymer, such as polycarbonate, which allows the user or care-giver to visualize placement of the hand within the chamber.

Thermal exchange member 104 may be disposed within appendage chamber 102 and may comprise a plastic, biocompatible metal, such as aluminum, metal alloy, or the like. Thermal exchange member 104 is configured to selectively heat or cool blood flowing through the AVA of the appendage disposed within appendage chamber 102. For example, thermal exchange member 104 may be configured to be heated to approximately 107.4° F., 108.4° F., 109.4° F., between 107-110° F., between 105-112° F., or between 100-120° F. and may be configured to be cooled to approximately 60.8° F., between 60-62° F., between 58-64° F., or between 58-95° F. In one embodiment, thermal exchange member 104 comprises a Peltier device configured to heat and/or cool thermal exchange member 104. Thermal exchange member 104 also may include suitable components for resistive heating such as a conductive wire configured to receive an electrical current and release heat. Thermal exchange member 104 may be shaped and sized to contact an appendage, for example, a palm of the hand. In one embodiment, thermal exchange member 104 includes palm pad 112 (shown in FIG. 1B) that extends outwardly from thermal exchange member 104 to promote enhanced contact with the palm.

Control panel 106 is configured to provide a user interface for a user and/or clinician or care-giver to control operations of apparatus 100. Control panel 106 may include buttons, assorted lighting sources, e.g., LEDs, and/or a display, e.g., an LCD or LED readout, that may be a touch screen. Illustratively, control panel 106 includes display 114, on/off button 116, on/off LED 118, ready symbol 120, ready LED 122, left button 124, right button 126, up button 128, down button 130, and accept button 132.

Appendage chamber 102 may include a plurality of feet 134, 136 coupled to appendage chamber base 138. Feet 134, 136 may be configured to be adjusted to raise or lower a portion of appendage chamber 102. For example, rear feet 136 may be adjusted to increase the distance between rear feet 136 and base 138, thereby raising the rear portion of apparatus 100. In one embodiment, feet 136 are coupled to base 138 via a threaded male member that is screwed into a threaded female member in appendage chamber 102 to adjust the distance between feet 136 and base 138. Advantageously, a user may adjust feet 136 such that appendage opening 108 is angled in a manner that the user may insert their hand into appendage opening 108 and comfortably rest their elbow on a surface, e.g., table, desk, or medical cart, holding apparatus 100.

Figure 1B:
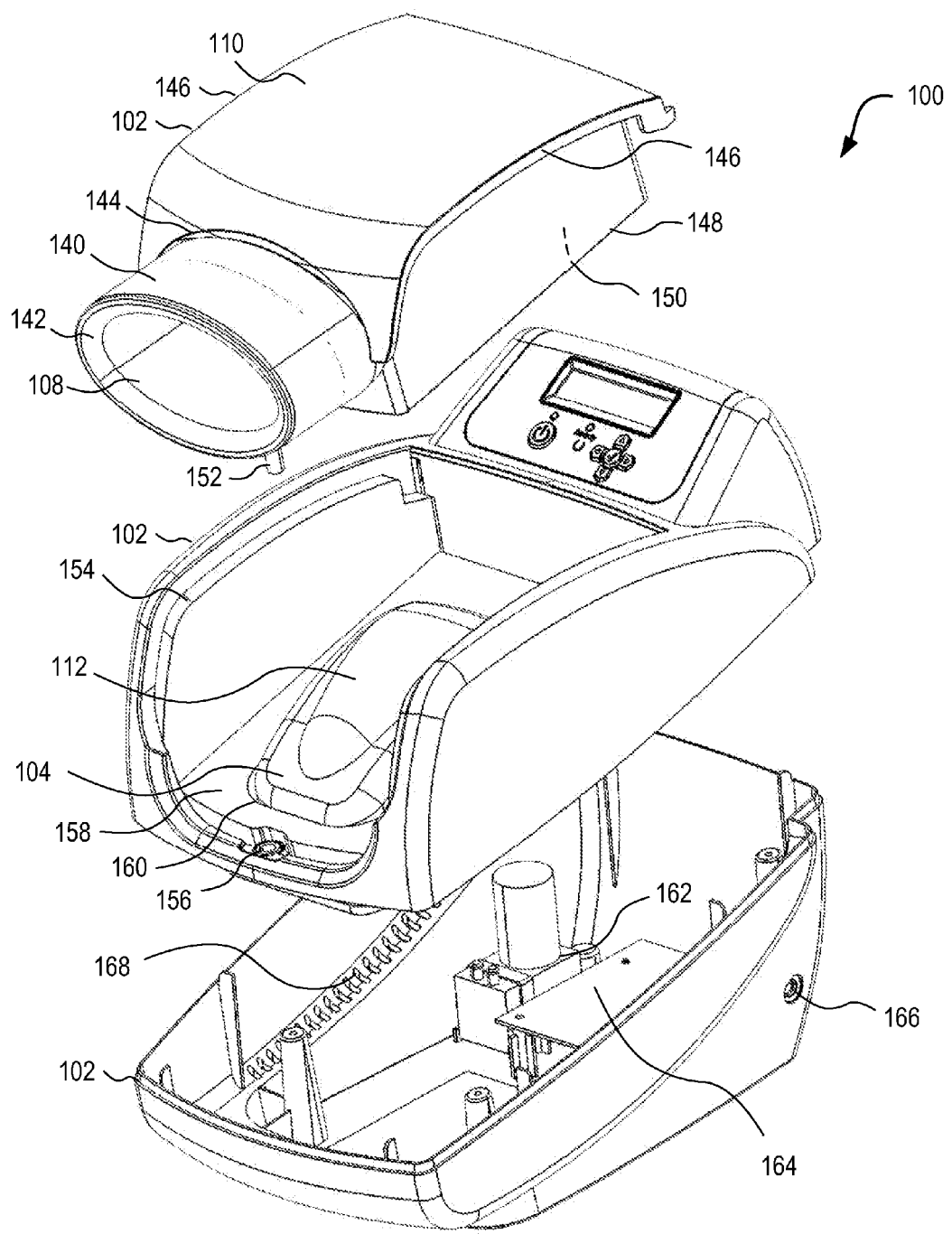
FIG. 1B is a perspective, partially exploded view of the exemplary apparatus of FIG. 1A.

As depicted in FIG. 1B, PCI 110 may include appendage opening 108, cuff 140, expandable cuff 142, cuff seal 144, PCI edges 146, PCI base 148, PCI base opening 150, and PCI positive pressure input 152. Cuff 140 may comprise a plastic, biocompatible metal, such as aluminum, metal alloy, or the like and is shaped and sized to accept an appendage through appendage opening 108. Illustratively, cuff 140 is elliptically shaped although, as would be understood by one of ordinary skill in the art, cuff 140 may take other shapes including a rectangle or a rectangle with rounded corners. Cuff 140 is coupled to expandable cuff 142. Expandable cuff 142 is configured to expand to seal around an appendage placed within PCI 110 through appendage opening 108. Expandable cuff 142 may comprise a rubber, such as latex, nitrile, or neoprene, and/or plastic, such as polyvinyl chloride, polyethylene, or polyurethane and may be between 5-20 mil thick, preferably about 8 mil. Cuff 140 may be coupled to the main body of PCI 110 via cuff seal 144. Cuff seal 144 is configured to couple cuff 140 to the main body of PCI 110, and may comprise a suitable adhesive material such as silicon. Cuff 140 optionally may be removable from PCI 110.

In accordance with one aspect of the present invention, PCI 110 is configured to be removable from appendage chamber 102. PCI 110 may be coupled to appendage chamber by placing PCI edges 146 on chamber ledges 154 of appendage chamber 102 such that PCI base 148 contacts appendage chamber 102, optionally at sealing pad 158, and thermal exchange member 104 is disposed within PCI base opening 150. PCI positive pressure input 152 is configured to be disposed within chamber aperture 156 of appendage chamber 102.

Apparatus 100 further may include sealing pad 158 that is configured to couple to PCI base 148 to maintain negative pressure within PCI 110. Sealing pad 158 is disposed within appendage chamber 102 and includes sealing pad opening 160 through which thermal exchange member 104 extends. Preferably, sealing pad 158 comprises a deformable, sponge-like or foam-like material that supports PCI base 148 when it contacts sealing pad 158 to create an air-tight seal. In one embodiment, sealing pad 158 includes a groove that accepts PCI base 148 therein.

Pressure source 162 and circuitry housing 164 having a programmable controller coupled thereto may be disposed within appendage chamber 102. Pressure source 162 is a suitable device for pumping fluid, e.g., air, and for creating and maintaining negative pressure in appendage chamber 102 at a suitable pumping rate, e.g., greater than about 4 liters per minute. In one embodiment, pressure source 162 is a diaphragm pump. Pressure source 162 may be configured to apply positive pressure to expand expandable cuff 142 to seal around an appendage placed therein by pumping a fluid into expandable cuff 142. Pressure source also may be configured to apply negative pressure within appendage chamber 102, including PCI 110, and to create an air-tight seal between PCI base 148 and sealing pad 158 when an appendage is placed therein. Pressure source 162 may be coupled to expandable cuff 142 via a pressure line coupled between pressure source 162 and PCI positive pressure input 152. In one embodiment, pressure source 162 is configured to maintain the negative pressure within the appendage chamber between −20 mmHg and −40 mmHg or between −1 mmHg and −50 mmHg. Pressure source 162 assists in maintaining vasodilation and to enhance the transfer to energy to an arteriovenous anastomosis vascular area of the appendage, e.g., located in the palm of a hand. The arteriovenous anastomosis vascular area may experience vasodilation from pre-treatment hyper-normothermia and/or heat delivered to the area from thermal exchange member 104 during treatment.

Appendage chamber 102 may include power interface 166 that connects to an AC or DC power source to power apparatus 100 and/or charge at least one battery within appendage chamber 102. In one embodiment, apparatus 100 is powered with at least one replaceable battery and power interface 166 may be omitted.

Appendage chamber 102 may further include a plurality of vent holes 168 configured to expel heat resulting from operation of apparatus 100 therethrough.

Figure 1C:
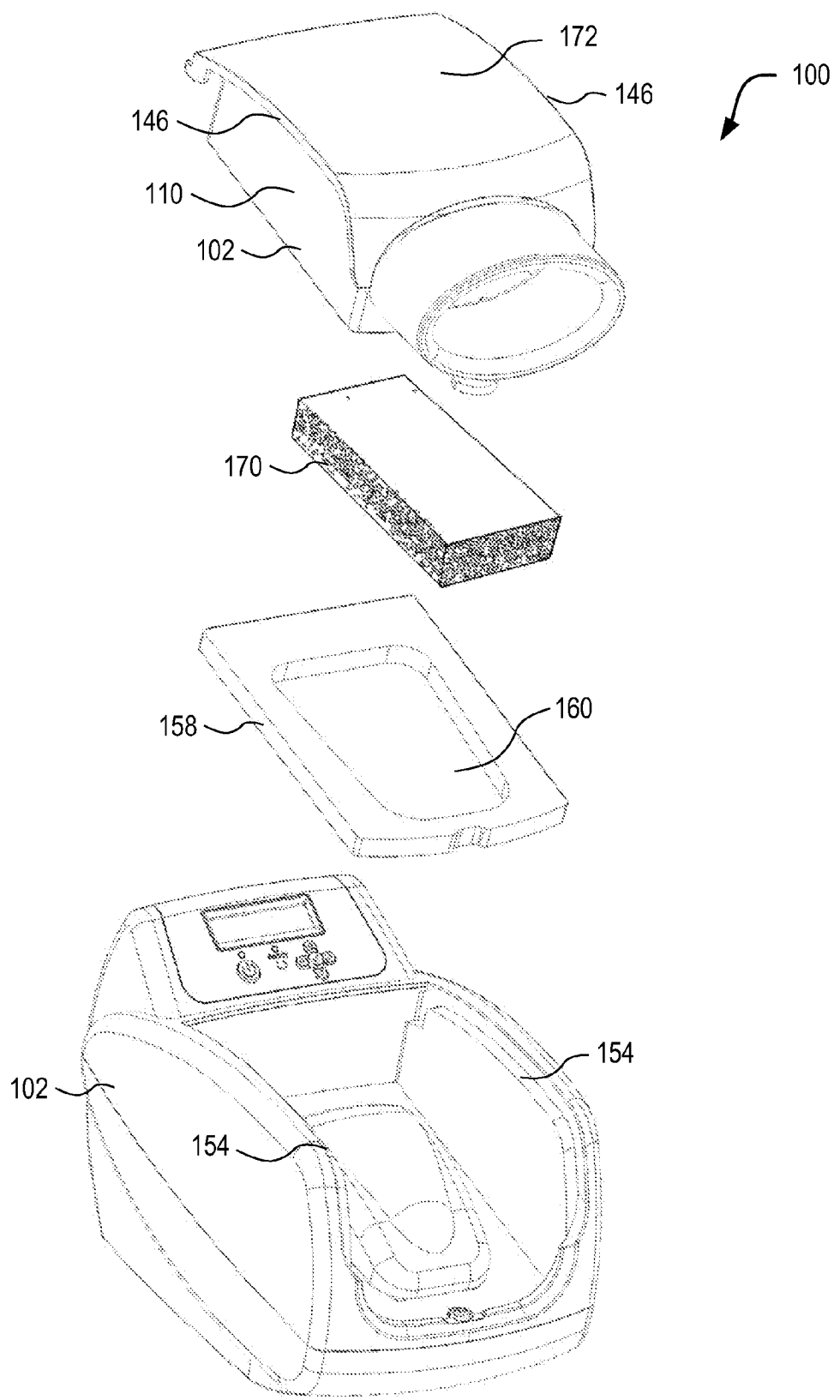
FIG. 1C is another perspective, partially exploded view of the exemplary apparatus of FIG. 1A.

As illustrated in FIG. 1C, apparatus 100 further may include deformable pad 170. Deformable pad 170 is configured to be disposed within appendage chamber 102, and specifically, within PCI 110. Deformable pad 170 may be coupled to upper surface 172 within PCI 110 via a suitable adhesive, VELCRO® coupling, or like. Preferably, deformable pad 170 comprises a deformable, sponge-like or foam-like material that contacts an appendage and appendage chamber 102, specifically upper surface 172 within PCI 110, to urge the appendage onto thermal exchange member 104. Advantageously, deformable pad 170 may be utilized to urge an appendage onto thermal exchange member 104 of a person unable to hold their appendage onto thermal exchange member 104 because, for example, they are unconscious. As shown in FIG. 1C, PCI 110, sealing pad 158, and/or deformable pad 170 may be removable from appendage chamber 102.

Figure 1D:
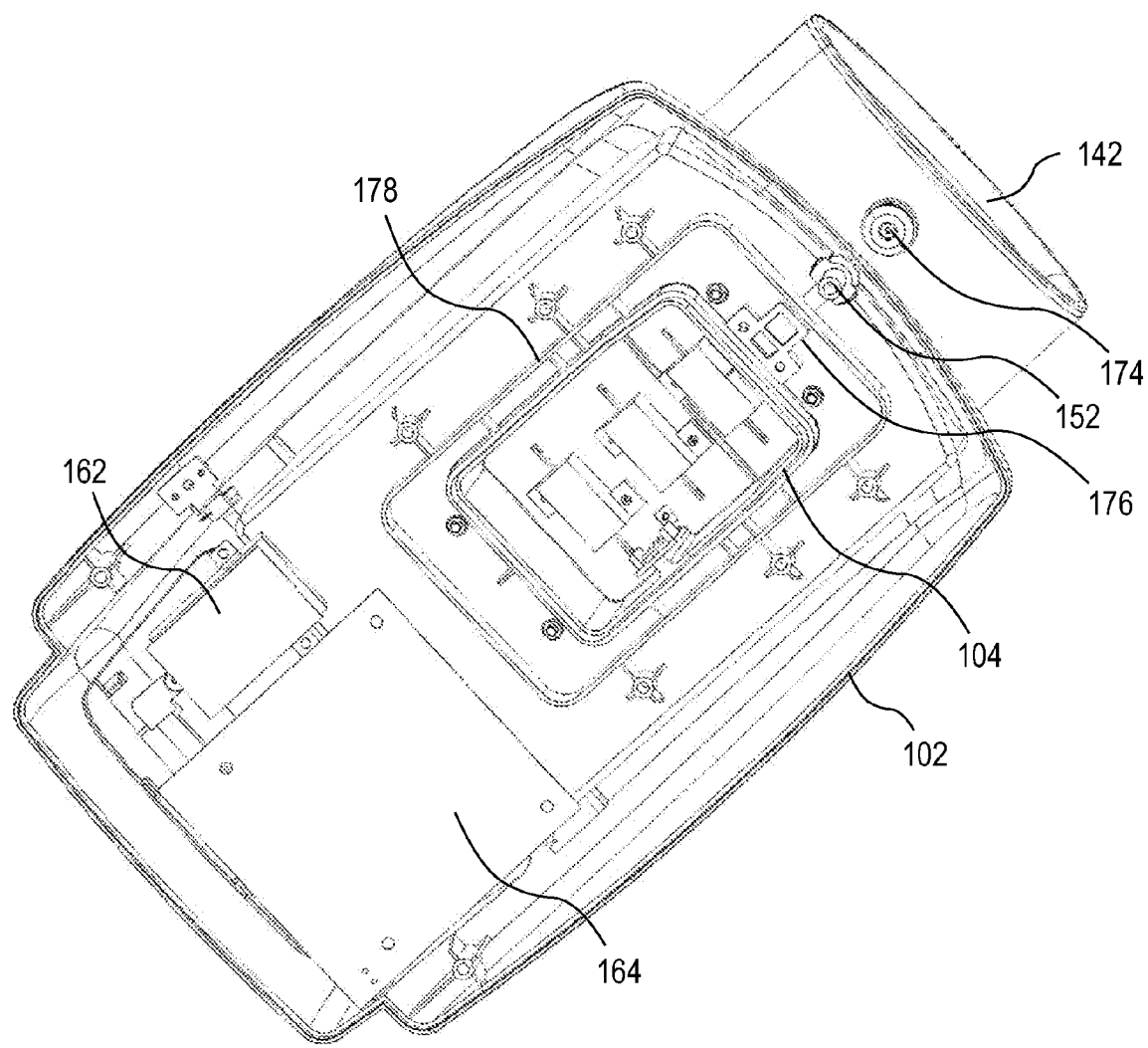
FIG. 1D is a bottom view of the exemplary apparatus of FIG. 1A with part of the lower housing removed for clarity.

FIG. 1D illustrates a bottom view of apparatus 100 with part of the lower housing and circuit board removed for clarity. Appendage chamber 102 includes relief valve 174 coupled to expandable cuff 142 and configured to release fluid, e.g., air, within expandable cuff 142 when relief valve 174 is depressed for pressure relief. Appendage chamber 102 further includes pressure pole 176 coupled to thermal exchange member 104. Pressure pole 176 displaces load sensor 190 (described below) when a force is applied to thermal exchange member 104, such that the applied force may be measured as described in detail below. Appendage chamber 102 further includes negative pressure opening 178 beneath thermal exchange member 104 such that pressure source 162 may apply negative pressure within appendage chamber 102, including within PCI 110, through negative pressure opening 178. Negative pressure opening 178 may span a substantial area beneath the base of the thermal exchange member 104, e.g., over 60% of the area.

In one embodiment, apparatus 100 further includes a circuit board disposed beneath thermal exchange member 104. The circuit board may permit application of negative pressure within appendage chamber 102, e.g., within PCI 110 through negative pressure opening 178, via pressure source 162.

Figure 2:
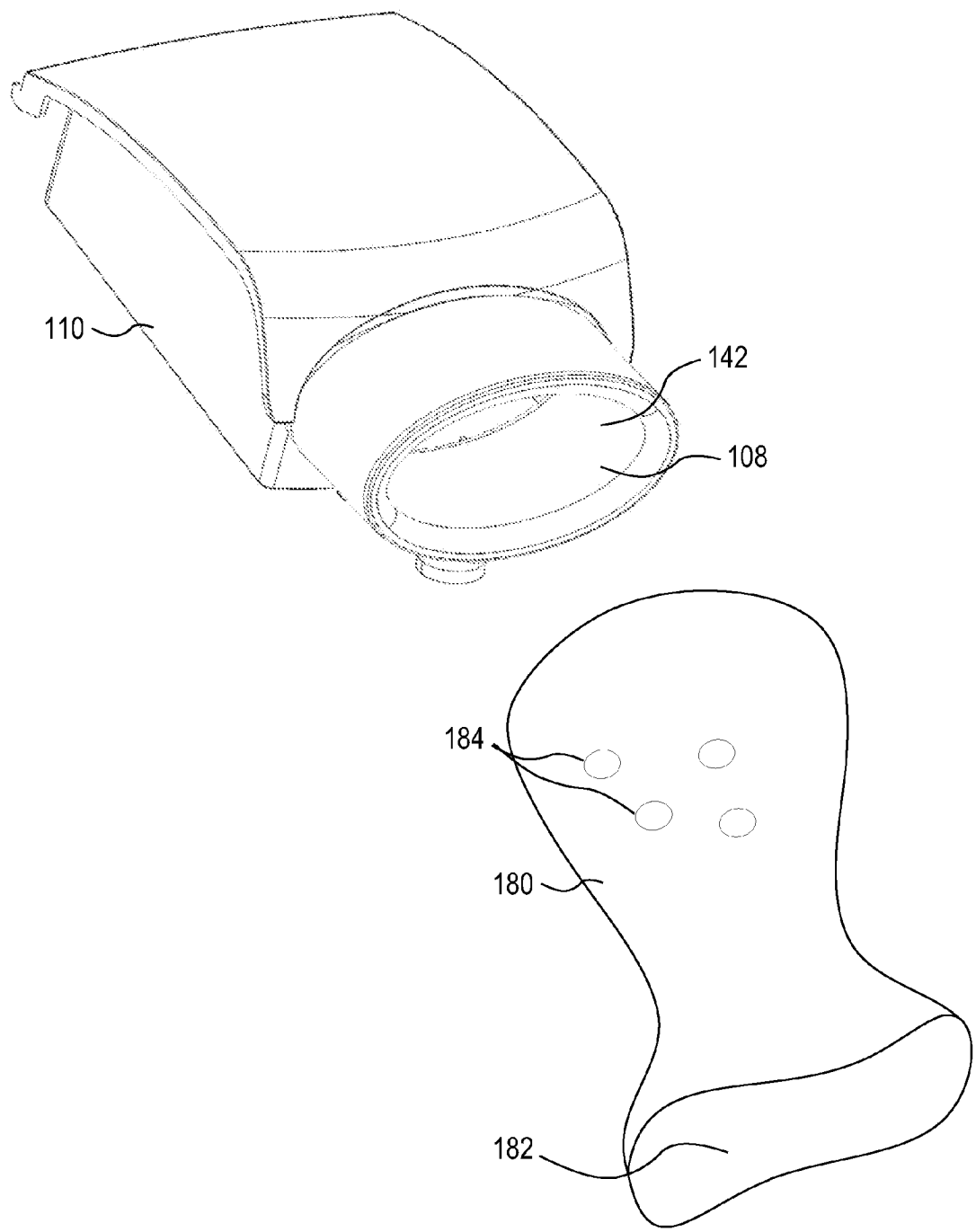
FIG. 2 is a perspective view of an exemplary pressure chamber insert and an exemplary flexible membrane constructed in accordance with one aspect of the present invention.

Referring now to FIG. 2, exemplary PCI 110 and flexible membrane 180 are illustrated in accordance with the present invention. Flexible membrane 180 is suitably sized to receive an appendage, e.g., a hand, wrist and forearm. Illustratively, flexible membrane 180 is generally tubular shaped, although it may be glove or mitt shaped, and includes membrane opening 182 that is configured to accept the appendage. Flexible membrane 180 may comprise a flexible and durable material, such as neoprene, that may be used with different patients. Alternatively, for sanitary purposes, flexible membrane 180 may be disposable and designed for one-time use. In this case, flexible membranes 180 having different sizes may be supplied with apparatus 100 to reduce cross-contamination if the device is used by multiple patients. Preferably, flexible membrane 180 comprises a light weight plastic, such as polyethylene or polyurethane, and is disposable after a single use reducing the potential for spread of bacteria or viruses in cases where multiple users use apparatus 100, such as hospital or nursing home settings. Provided that the material comprising flexible membrane 180 is sufficiently thin, e.g., 0.5 mil, flexible membrane 180 is expected to provide adequate heat transfer between the palm of the hand and thermal exchange member 104. Flexible membrane 180 may include pressure equalizing vent(s) 184 configured to permit a fluid, e.g., air, to be drawn from within flexible membrane 180 through vents 184 as negative pressure is applied via pressure source 162 to create a negative pressure environment within flexible membrane 180. Flexible membrane 180 is further configured to conform to expandable cuff 142 as pressure source 162 applies positive pressure to expand expandable cuff 142 when flexible membrane is disposed within appendage opening 108.

Flexible membrane 180 may further include a sealing member, e.g., a rubber O-ring, an elastic band, an attached VELCRO® strap, or the like, configured to tighten flexible membrane 180 around a portion of a user's appendage, e.g., wrist or forearm.

Flexible membrane 180 is configured to be at least partially disposed within appendage chamber 102, and specifically PCI 110, and may be removable from appendage chamber 102.

Figure 3:
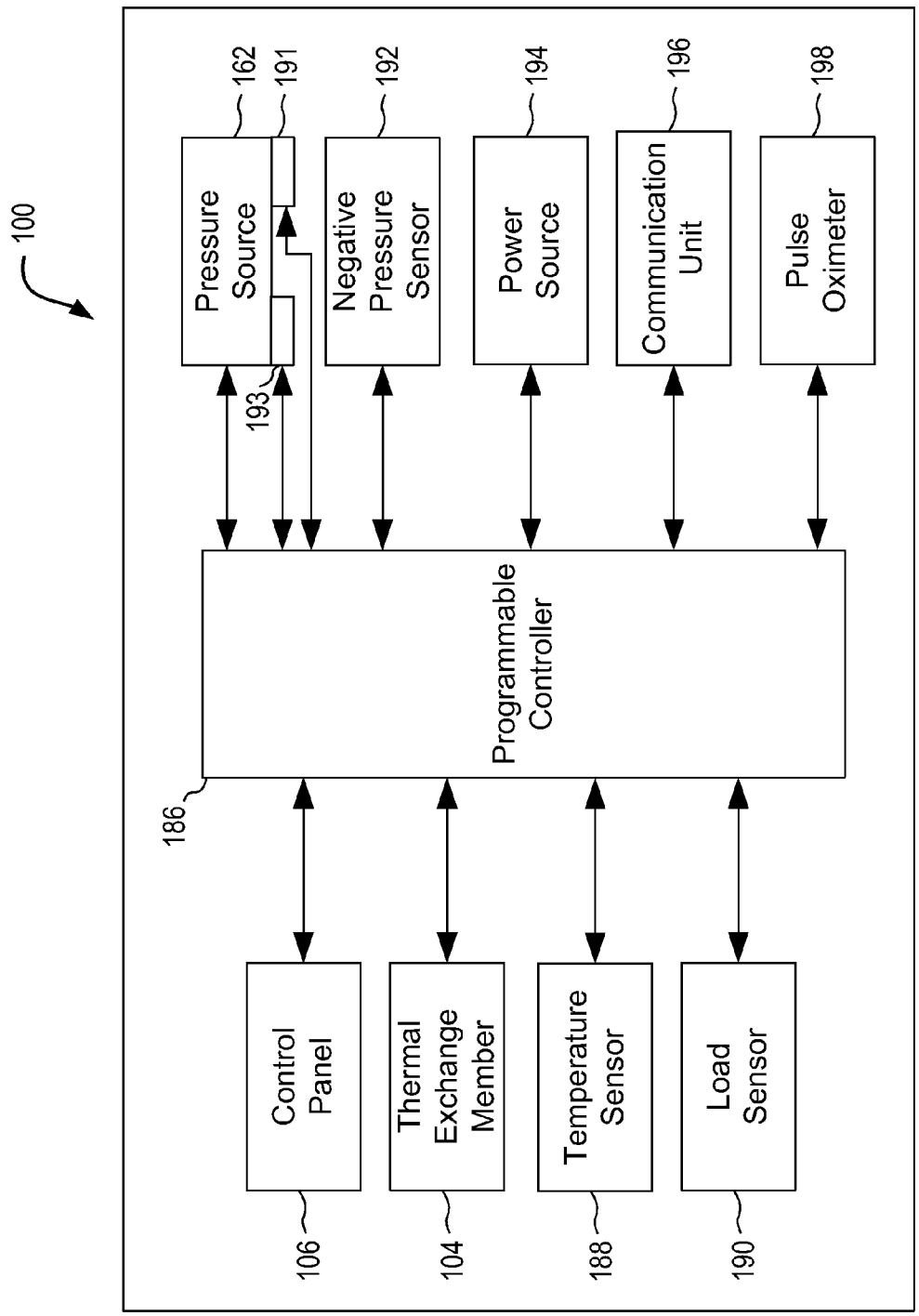
FIG. 3 is a schematic view of an apparatus for treating a condition using thermal energy constructed in accordance with one aspect of the present invention.

Referring now to FIG. 3, a schematic illustrating the internal components of the embodiment of apparatus 100 is described. Programmable controller 186 may be electrically coupled to, and configured to control, thermal exchange member 104, control panel 106, temperature sensor 188, load sensor 190, pressure source 162, negative pressure sensor 192, power source 194, communication unit 196, and/or pulse oximeter 198.

Programmable controller 186 may include one or more microprocessors, controllers, digital signal processors (DSPs), application specific integrated circuits (ASICs), field-programmable gate arrays (FPGAs), or equivalent discrete or integrated digital or analog logic circuitry, and the functions attributed to programmable controller 186 herein may be embodied as software, firmware, hardware, or any combination thereof. Programmable controller 186 may include a memory for storing data related to use of apparatus 100, such as user input, treatment times, treatment settings, detected errors, and the like. The memory may store program instructions that, when executed by programmable controller 186, cause programmable controller 186 and apparatus 100 to provide the functionality ascribed to them herein. The memory of programmable controller 186 also may store software downloaded thereon or implemented as a program product and stored on a tangible storage device such as machine-readable medium, e.g., tape, compact disk (CD), digital versatile disk (DVD), blu-ray disk (BD), external nonvolatile memory device, USB, cloud storage, or other tangible storage medium. The software may include computer executable instructions for controlling apparatus 100.

Programmable controller 186 also may store in its memory therapy programs directed to treatment of specific maladies. For example, an embodiment of apparatus 100 intended for use in a nursing home setting may include programs for increasing whole body circulation to address neurological ailments, such as migraine headaches, or circulatory issues, such as chronic wounds or reduced peripheral blood flow resulting from diabetes or immobility. In this context, apparatus may be used by a number of nursing home residents to provide relief from such ailments, and include preprogrammed therapeutic regimes (e.g., appropriate temperature adjustments for preselected durations) suitable for treating such residents. Preselected programs stored in apparatus 100 may be loaded at the manufacturer, or generated using a suitable software program on a conventional personal computer and then uploaded to memory associated with programmable controller 186 via a data port, e.g., USB port, on appendage chamber 102 or communication unit 196, described below. The data port further may be used to retrieve and/or store data on a tangible storage device related to use of apparatus 100, such as user input, treatment times, treatment settings, detected errors, and the like.

Programmable controller 186 preferably also includes preprogrammed safety features, e.g., that shutdown the device if the apparatus sensors, such as the temperature and negative pressure sensors, fail or become disconnected. Programmable controller 186 also may include an error circuit that displays error codes on control panel 106.

The electronics of apparatus 100 are coupled to control panel 106, so that programmable controller 186 actuates apparatus 100 in accordance with input commands or selection of pre-programmed therapy regimes input via control panel 106. For example, referring to FIG. 1A, when programmable controller 186 detects that left button 124 or right button 126 is pressed, programmable controller 186 directs thermal exchange member 104 to decrease or increase temperature, respectively. As another example, when programmable controller 186 detects that up button 128 or down button 130 is pressed, programmable controller 186 directs a clock application to increase or decrease, respectively, a countdown timer for treatment.

Referring back to FIG. 3, programmable controller 186 is configured to direct thermal exchange member 104 to heat or cool to a temperature responsive to user input at control panel 106 or to a preselected therapy regime. In one embodiment, programmable controller 186 is programmed to heat thermal exchange member to a high, medium, or low temperature, e.g., 109.4° F., 108.4° F., or 107.4° F., respectively, based on user input received at control panel 106. Programmable controller 186 further may include a clock application that directs thermal exchange member to heat or cool at the temperature for a time, e.g., 5, 10, 15, 20, 25, or 30 minutes, responsive to user input at control panel 106 or to a preselected therapy regime.

Temperature sensor 188 is a suitable temperature sensor, e.g., a thermocouple, that may be disposed adjacent to or within thermal exchange member 104. Temperature sensor 188 is configured to sense a temperature at thermal exchange member 104. Temperature sensor 188 may be operatively coupled to programmable controller 186 to regulate heating or cooling to maintain thermal exchange member 104 at substantially a target temperature that may be preprogrammed or input via control panel 106.

Load sensor 190 is a suitable force sensor, e.g., a load cell or pressure transducer, and may be disposed adjacent to or within thermal exchange member 104. Load sensor 190 is configured to measure a force, e.g., a force of a user's hand, applied to thermal exchange member 104. Advantageously, thermal exchange member 104 and load sensor 190 are configured to accommodate many different sizes of hands, including those of unconscious patients, while minimizing the risks of discomfort or vasoconstriction. Force measured at load sensor 190 may be used by programmable controller 186 to determine if a hand is placed too lightly on thermal exchange member 104, thereby reducing energy transfer, or placed too heavily, thereby inducing vasoconstriction of the vasculature of the palm, also reducing energy transfer. As explained below, an alert at control panel 106 may be audibly or visibly displayed if the measured force is not within a predetermined range, e.g., too high or too low, to alert a user/caregiver/physician.

As explained above, pressure source 162 is configured to apply positive pressure to expand expandable cuff 142 and to apply negative pressure within appendage chamber 102 and to assist in maintaining vasodilatation of, and to enhance energy transfer to, an appendage when placed within appendage chamber 102. In one embodiment, pressure source 162 is configured to apply negative pressure within appendage chamber 102 and, specifically, within PCI 110 to create an air-tight seal between PCI base 148 and sealing pad 158. Pressure source 162 may be coupled to appendage chamber 102 via a pressure line that is coupled to negative pressure check valve 191. Negative pressure check valve 191 is configured to open to allow the release of excess negative pressure from pressure source 162. In addition, pressure source 162 may be coupled to expandable cuff 142 via a pressure line that is coupled to positive pressure check valve 193. Positive pressure check valve 193 is configured to open to allow the release of excessive positive pressure from expandable cuff 142.

Negative pressure sensor 192 may be coupled to appendage chamber 102. Negative pressure sensor 192 is a suitable pressure sensor and is configured to measure the pressure within appendage chamber 102 and specifically, within PCI 110, to output a signal to programmable controller 186 that is used to achieve a preselected negative pressure, e.g., between −20 mmHg and −40 mmHg or between −1 mmHg and −50 mmHg, within PCI 110. Programmable controller 186 is configured to monitor application of negative pressure within PCI 110 responsive to pressure measured by negative pressure sensor 192. In one embodiment, pressure source 162 is coupled to a pressure relief valve, e.g., via a pressure line, that is configured to release excess pressure at a predetermined pressure, e.g., lower than −50 mm Hg, −80 mm Hg, or −100 mm Hg, should negative pressure sensor 192 or programmable controller 186 malfunction.

Power source 194 may be a port, e.g., power interface 166, to allow apparatus 100 to be plugged into a conventional wall socket, e.g., via a cord with an AC to DC power converter, for powering components within the housing. Alternatively, power source 194 may be a suitable battery such as a replaceable battery or rechargeable battery and apparatus may include circuitry for charging the rechargeable battery, and a detachable power cord.

Communication unit 196 is configured to transmit information, such as user input, treatment times, treatment settings, detected errors, and the like, to a remote location such as a doctor workstation. Communication unit 196 is configured for wired and/or wireless communication over a network such as the Internet or a telephone network using techniques known in the art. Advantageously, communication unit 196 permits a doctor, caregiver, user, and the like to monitor use of apparatus 100.

Optionally, apparatus 100 may include pulse oximeter 198 configured to monitor oxygen saturation of a user's blood using components known in the art. In one embodiment, components including a light emitter, e.g., a pair of LEDs, and a light receiver, e.g., a photodiode, are disposed within appendage chamber 102 for monitoring oxygen saturation and blood volume during a treatment by apparatus 100. Programmable controller 186 may direct control panel 106 to display pulse oximetry information, e.g., oxygen saturation levels, pulse rate, photoplethysmograph, etc., or may direct communication unit 196 to transmit the pulse oximetry information to a remote location.

In alternative embodiments, one or more of the components supplied within appendage chamber 102 may be omitted. For example, an embodiment of apparatus 100 suitable for use in a hospital, where suction lines are readily available in the patient rooms, may omit pressure source 162 and instead use the "house" suction system.

Methods of Using the Apparatus

Methods of using apparatus for the therapeutic application of thermal energy will now be described with reference to FIGS. 1A through 3.

Apparatus 100 may be used to treat a variety of conditions believed to arise from deficiencies of the autoimmune, circulatory, lymphatic and endocrine systems, and which may beneficially impact neurological deficits as well. It is expected, for example, that use of the apparatus of the present invention may treat or alleviate a variety of ailments as described in U.S. Patent Application Publication No. 2012/0191022 to Muehlbauer, and others including: improved healing for acute and chronic wounds and post-operative conditions; relief for respiratory conditions such as asthma; sleeping conditions such as snoring and sleep apnea; metabolic disorders such as hypothyroidism; obesity; chronic fatigue syndrome; certain autoimmune disorders; Raynaud's phenomenon; hot flashes; edema; renal disease; cirrhosis; allergies; neurological maladies such as Parkinson's disease, diabetic neuropathy, migraines, Alzheimer's disease, bipolar disorder, schizophrenia, attention deficit disorder (ADD), attention deficit hyperactivity disorder (ADHD), obsessive compulsive disorder (OCD), and Autism; circulatory disorders associated with vasoconstriction such as hypertension, carpal tunnel syndrome, trigger finger, and arthritis; diabetes; dermatological disorders associated with restricted blood flow to the skin such as eczema; disorders known to disrupt thermoregulatory processes such as stress and anxiety; neurodegenerative conditions such as multiple sclerosis and fibromyalgia; increased fetal circulation during pregnancy; and sequalae of chemotherapy (affecting digestion) and irritable bowel syndrome (affecting bowel regularity). Apparatus 100 also may be used to enhance delivery of drugs by increasing body circulation.

Applicant has discovered that apparatus 100 also may be used to reduce core body temperature for treatment of heart attack, stroke, heat stroke, and fever including fever not resulting from an immune response. Applicant has additionally discovered that apparatus 100 may be used to adjust blood viscosity to alleviate a symptom(s) associated with all diseases or conditions associated with systemic inflammation or hyperviscosity of the blood.

In operation, a user or clinician activates apparatus 100 using control panel 106 and selects a heating or cooling mode, or if available, one a plurality of preprogrammed therapeutic regimes. Pushing on/off button 116 activates power to apparatus 100 via power source 194 and turns on on/off LED 118 to indicate that the apparatus is powered on. After the controller power is activated, the system begins preheating thermal exchange member 104, LED 122 is activated to amber. Once thermal exchange member 104 is preheated to the desired temperature, ready LED 122 is activated to green. In one embodiment, if a user desires to enter a standby mode, the user may provide certain user input at control panel 106, e.g., holding down accept button 132 and pressing on/off button 116 at the same time. In standby mode, programmable controller 186 directs thermal exchange member 104 to heat to a standby temperature, e.g., 100° F., for a predetermined standby time, e.g., 4 hours, or until the user provides input to deactivate standby mode.

Before, during, or after the preheat process, a user may provide user input at control panel 106 regarding selection of a treatment time, treatment temperature, and/or therapy regime selection. A user may insert their appendage into flexible membrane 180 via membrane opening 182. The user then may contact a portion of the appendage, e.g., a palm of their hand, to thermal exchange member 104.

Display 114 of control panel 106 may display a request that the user press accept button 132 when flexible membrane 180 is secured around the appendage and positioned with appendage chamber 102. Once accept button 132 is pressed, programmable controller 186 directs pressure source 162 to apply positive pressure to expandable cuff 142 to seal around the appendage and to apply negative pressure within appendage chamber 102, for example, in PCI 110 via negative pressure opening 178. After a predetermined amount of time, e.g., 1 minute, programmable controller 186 communicates with negative pressure sensor 192 regarding pressure sensed by negative pressure sensor 192. If the pressure indicates that a suitable pressure was not reached, programmable controller 186 directs control panel 106 to alert the user and may power down apparatus 100. Alternatively, if the pressure indicates that a suitable pressure was reached, the programmed routine continues.

Programmable controller 186 may monitor the force applied by the appendage to thermal exchange member 104 via load sensor 190 to calibrate the appropriate force for the appendage on an individual basis for each user. In one embodiment, programmable controller 186 reads the force values measured at load sensor 190 a predetermined number of times, e.g., 10 times, at a predetermined sampling rate, e.g., 0.25 seconds between samples. If all of the measured force values are within a predetermined threshold, e.g., within 75% of the high/low threshold for the average value of the measured force values, then the calibration will pass. If one of the measured force values is outside the predetermined threshold, the calibration will fail and programmable controller 186 will direct display 114 to display that the user should lift the appendage off thermal exchange member 104 for recalibration.

After the calibration process is completed, a user may begin to receive treatment at the selected temperature setting and for the selected time. Thermal exchange member 104 may deliver heating or cooling to blood flowing through the AVA at a temperature and for a duration sufficient to alleviate symptoms associated with a condition or disease. In one embodiment, display 114 displays a countdown timer indicative of the time remaining in a treatment and an indication of the current temperature setting.

During treatment, programmable controller 186 polls control panel 106 to determine if a user provides input during treatment and, if so, directs the appropriate component to respond to the user input. Also during treatment, programmable controller 186 polls temperature sensor 188, load sensor 190, and negative pressure sensor 192. If temperature sensor 188 senses that thermal exchange member 104 is not maintaining the selected temperature, programmable controller 186 directs display 114 to display a heater error message. If load sensor 190 senses that the measured force falls outside a predetermined range from the calibrated force value, programmable controller 186 directs control panel 106 to audibly alert and directs display 114 to display a message notifying a user to press down on thermal exchange member 104 if the force is too low or display a message notifying a user to lift up from thermal exchange member 104 if the force is too high. If negative pressure sensor 192 senses that the pressure within appendage chamber is outside a predetermined range, programmable controller 186 directs control panel 106 to audibly or visibly alert a user that the pressure seal is lost. In addition, as described in detail below, programmable controller 186 may monitor pressure measured by negative pressure sensor 192 and direct positive pressure source to expand expandable cuff 142 if the measured pressure is outside a predetermined range, e.g., above a predetermined pressure.

When the time for treatment is completed, programmable controller 186 directs apparatus 100 to power down one or more components, e.g., thermal exchange member 104, negative pressure sensor 192, power source 194, if standby mode is off and directs apparatus 100 to enter standby mode if standby mode is on keeping thermal exchange member 104 in preheat mode. The user may then break expandable cuff 142 seal by depressing relief valve 174 and withdrawing the appendage from appendage chamber 102.

Figure 4:
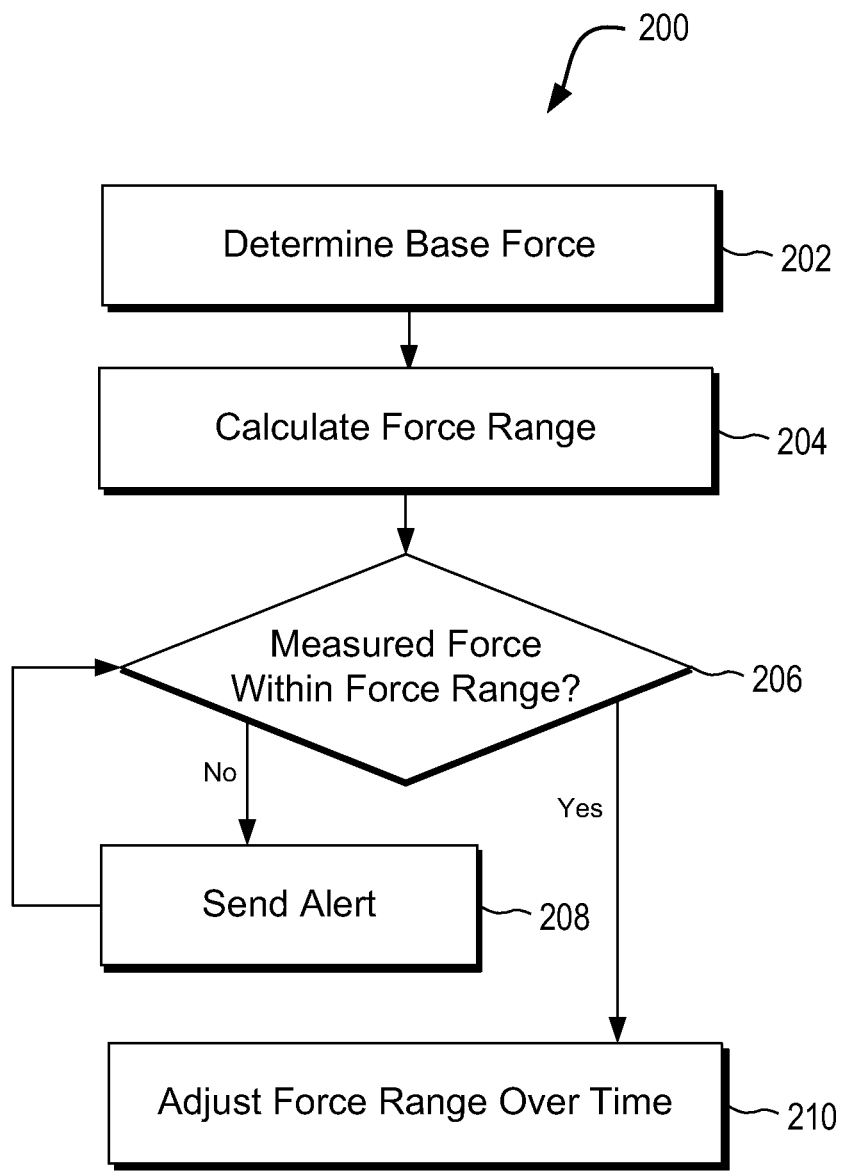
FIG. 4 is a flowchart depicting a method for determining and adjusting a force range measured at the thermal exchange member in accordance with the methods of the present invention.

Referring now to FIG. 4, apparatus and method 200 for determining and adjusting a force range measured at thermal exchange member 104 are now described. As will be apparent to one of ordinary skill in the art, method 200 may be embodied in program instructions stored on the memory of programmable controller 186 of FIG. 3 that, when executed by programmable controller 186, cause programmable controller 186 and apparatus 100 to provide the functionality ascribed to them herein. The program instructions may be firmware or software downloaded onto the memory of programmable controller 186 or implemented as a program product and stored on a tangible storage device such as machine-readable medium, e.g., tape, compact disk (CD), digital versatile disk (DVD), blu-ray disk (BD), external nonvolatile memory device, USB, cloud storage, or other tangible storage medium.

At 202, programmable controller 186 determines a base force measured using load sensor 190 of an appendage on thermal exchange member 104. In one embodiment, the base force is determined to be the average of the measured force values from the calibration process described above. In that embodiment, programmable controller 186 reads the force values measured at load sensor 190 a predetermined number of times, e.g., 10 times, at a predetermined sampling rate, e.g., 0.25 seconds between samples. If all of the measured force values are greater than zero and within a predetermined threshold, e.g., within 75% of the high/low threshold for the average value of the measured base force values, then the calibration will pass and the base force will be that average value. If one of the measured force values is outside the predetermined threshold, the calibration will fail and programmable controller 186 will direct control panel 106 to audibly alert and direct display 114 to display a message notifying a user to press down on thermal exchange member 104 for recalibration if the force is too low or display a message notifying a user to lift up from the thermal exchange member 104 for recalibration if the force is too high.

At 204, programmable controller 186 calculates and sets a force range using the base force measured at 202. In one embodiment, programmable controller 186 calculates and sets the force range using a lookup table stored in the controller's memory that includes an optimal energy transfer range including a low threshold and a high threshold for a base force. In another embodiment, programmable controller 186 calculates and sets the force range by multiplying the base force by a predetermined number, e.g., 0.75, to calculate the low threshold and multiplying the base force by a different predetermined number, e.g., 1.25, to calculate the high threshold of the force range. In yet another embodiment, programmable controller 186 calculates and sets the force range by subtracting a predetermined number from the base force to calculate the low threshold and adding a predetermined number, which may be the same or different, to the base force to calculate the high threshold of the force range.

At 206, programmable controller 186 monitors whether the force of the appendage on thermal exchange member 104 measured by load sensor 190 falls within the force range calculated and set at 204. Preferably, programmable controller 186 monitors the force of the appendage during a treatment at a predetermined sampling rate.

If programmable controller 186 detects that the force measured in 206 is outside the force range, programmable controller 186 directs apparatus 100 to send an alert to the user/physician/caregiver, at 208. Sending an alert may include directing control panel 106 to visibly and/or audibly alert the user. In one embodiment, if programmable controller 186 detects that the measured force is below the force range, display 114 displays text to request a user to press down and if programmable controller 186 detects that the measured force is above the force range, display 114 displays text to request a user to lift up. Sending an alert may also include shutting down power to one or more components to apparatus 100 such thermal exchange member 104, pressure source 162, and/or power source 194.

After alerting the user/physician/caregiver in 208, programmable controller 186 returns to 206 to monitor whether the measured force of the appendage is within the force range. If not, programmable controller 186 may continue to send alerts to the user/physician/caregiver and, in one embodiment, may shut down one or more components to apparatus 100 if a predetermined number of display alerts are sent.

If programmable controller 186 detects that the force measured in 206 is within the force range, programmable controller 186 adjusts the force range over time, at 210. In one embodiment, programmable controller 186 adjusts the force range over time using an algorithm stored in the controller's memory. Programmable controller 186 may adjust the force range after a predetermined time interval, e.g., every 5 minutes, using a lookup table stored in the controller's memory. Advantageously, adjusting the force range over time accommodates for ambient temperature variations caused by heating or cooling thermal exchange member 104.

Figure 5:
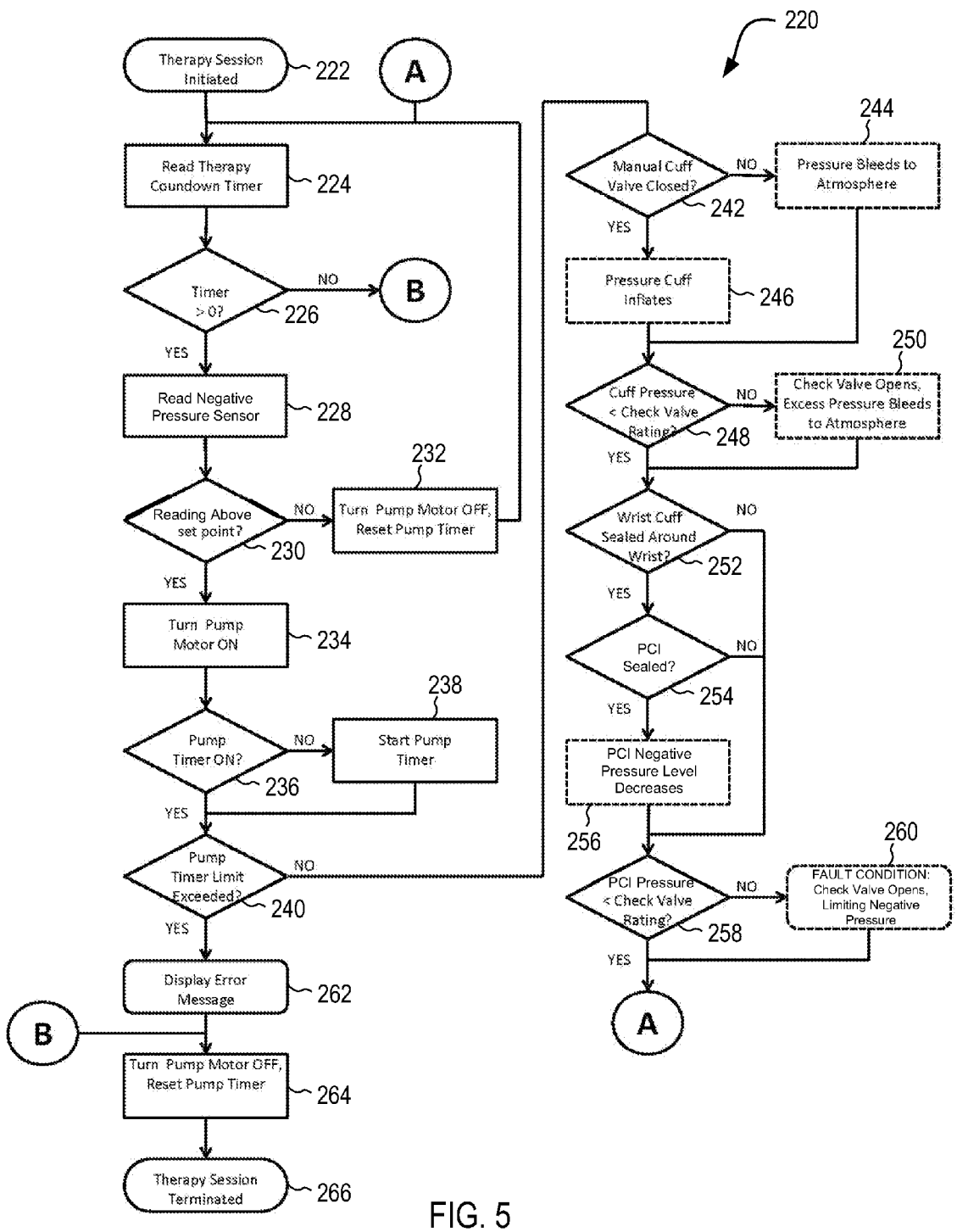
FIG. 5 is a flowchart depicting a method for applying positive and negative pressures in accordance with the methods of the present invention.

Referring now to FIG. 5, apparatus and method 220 for applying positive and negative pressures within apparatus 100 are now described. As will be apparent to one of ordinary skill in the art, method 220 may be embodied in program instructions stored on the memory of programmable controller 186 of FIG. 3 that, when executed by programmable controller 186, cause programmable controller 186 and apparatus 100 to provide the functionality ascribed to them herein. The program instructions may be firmware or software downloaded onto the memory of programmable controller 186 or implemented as a program product and stored on a tangible storage device such as machine-readable medium, e.g., tape, compact disk (CD), digital versatile disk (DVD), blu-ray disk (BD), external nonvolatile memory device, USB, cloud storage, or other tangible storage medium.

At 222, apparatus 100 is powered on and a therapy session is initiated based on user input, as described above. For example, a user may select a treatment time, a heating or cooling mode, or if available, a plurality of preprogrammed therapeutic regimes.

Programmable controller 186 reads the therapy countdown timer of the clock application, at 224. At 226, if the countdown timer is at zero, programmable controller 186 directs apparatus 100 to B, shown in FIG. 5, after which programmable controller 186 directs the pump motor of pressure source 162 to turn off, directs the pump timer to reset, and terminates the therapy session, as described below. Alternatively, if the countdown timer is greater than zero, programmable controller 186 reads the pressure measured by negative pressure sensor 192, at 228. If, at 230, the measured pressure read by programmable controller 186 is less than or equal to a predetermined pressure, programmable controller 186 directs the pump motor of pressure source 162 to turn off, directs a pump timer to reset, and returns to 224, at 232. On the other hand, if the measured pressure read by programmable controller 186 is greater than a predetermined pressure, programmable controller 186 directs the pump motor of pressure source 162 to turn on, at 234.

At 236, programmable controller 186 polls a pump timer application to determine whether the pump timer is on. If the pump timer is not on, programmable controller 186 directs the pump timer to turn on, at 238. If the pump timer is on, programmable controller 186 determines whether the pump timer limit is exceeded, at 240. If programmable controller 186 determines that the pump timer limit is not exceeded, a user may determine whether relief valve 174 at expandable cuff 142 is closed, at 242. If relief valve 174 is open, fluid is released from expandable cuff 142 via relief valve 174, at 244. Programmable controller 186 directs pressure source 162 to apply positive pressure to expand expandable cuff 142, at 246 and negative pressure within appendage chamber 102 and specifically, within PCI 110.

At 248, positive pressure check valve 193 determines whether pressure within expandable cuff 142 is greater than the rating pressure for positive pressure check valve 193 coupled to expandable cuff 142. If the pressure within expandable cuff 142 is greater than or equal to the check valve rating pressure, positive pressure check valve 193 will open to release fluid thereby reducing pressure within expandable cuff 142, at 250. If the pressure within expandable cuff 142 is less than the check valve rating pressure, programmable controller 186 directs pressure source 162 to apply positive pressure to expand expandable cuff 142, at 246 and negative pressure within appendage chamber 102 and specifically, within PCI 110.

If, at 252, expandable cuff 142 is sealed and, at 254, PCI 110 is sealed to sealing pad 158, programmable controller 186 directs pressure source 162 to apply negative pressure within appendage chamber 102, including within PCI 110, at 256. At 258, if pressure within appendage chamber 102, including PCI 110, is less than the check valve rating pressure for negative pressure check valve 191 coupled to pressure source 162 and appendage chamber 102, including PCI 110, negative pressure check valve 191 will open to release fluid thereby increasing pressure within appendage chamber 102, including PCI 110, at 260. If the pressure within appendage chamber 102, including PCI 110, is greater than the negative pressure check valve 191 rating pressure, programmable controller 186 returns to A in FIG. 5.

If, at 240, programmable controller 186 determines that the pump timer limit is exceeded, programmable controller directs display 114 to display an error message, at 262. Then, after B, programmable controller 186 directs the pump motor of pressure source 162 to turn off and directs the pump timer to reset, at 264. Finally, at 266, programmable controller 186 directs on or more components of apparatus 100 to shut down and terminates the therapy session.

Figure 6:
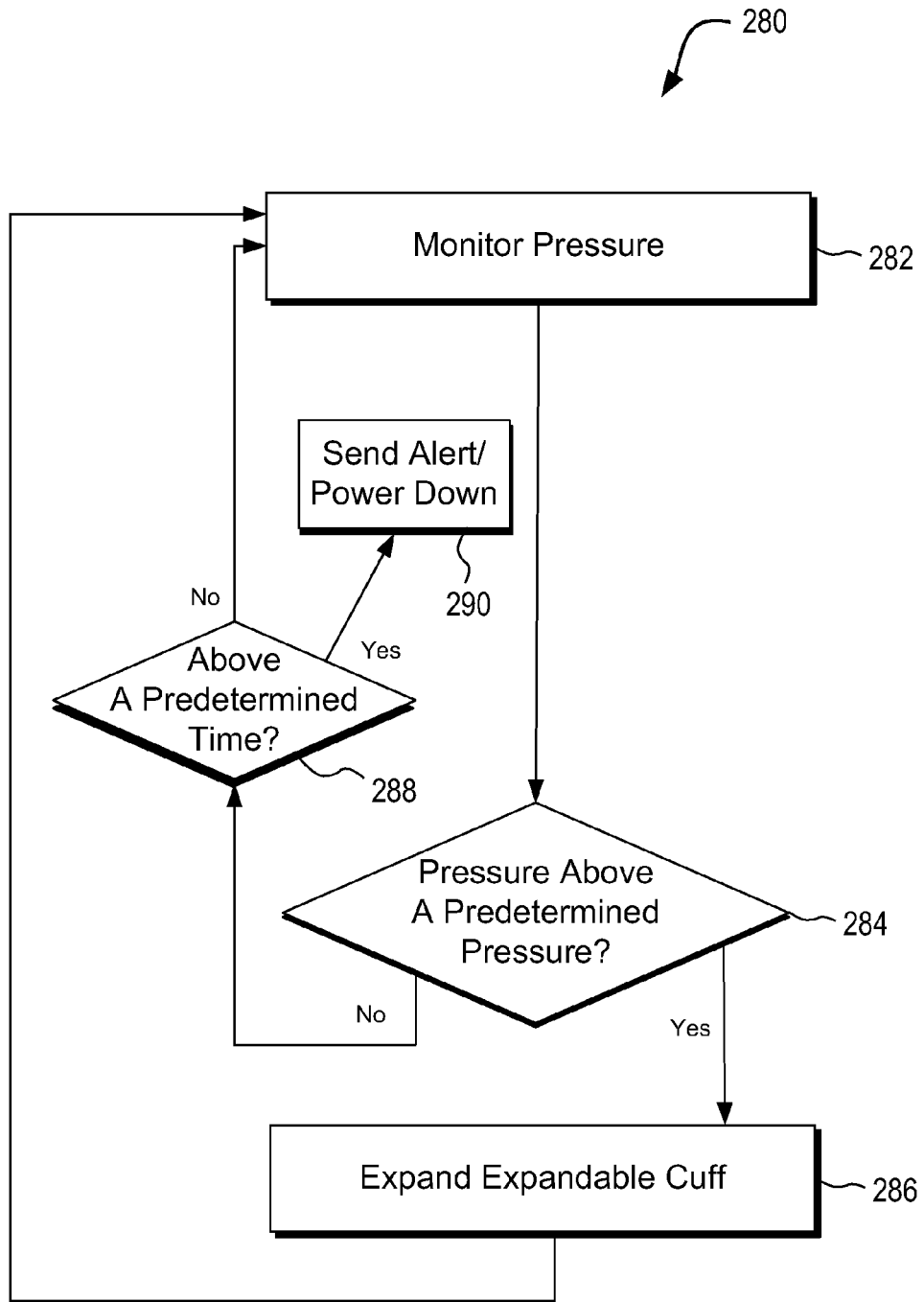
FIG. 6 is a flowchart depicting a method for monitoring pressure and adjusting pressure within the apparatus in accordance with the methods of the present invention.

Referring now to FIG. 6, apparatus and method 280 for monitoring pressure and adjusting pressure within apparatus 100 are now described. As will be apparent to one of ordinary skill in the art, method 280 may be embodied in program instructions stored on the memory of programmable controller 186 of FIG. 3 that, when executed by programmable controller 186, cause programmable controller 186 and apparatus 100 to provide the functionality ascribed to them herein. The program instructions may be firmware or software downloaded onto the memory of programmable controller 186 or implemented as a program product and stored on a tangible storage device such as machine-readable medium, e.g., tape, compact disk (CD), digital versatile disk (DVD), blu-ray disk (BD), external nonvolatile memory device, USB, cloud storage, or other tangible storage medium.

At 282, programmable controller 186 monitors the pressure within appendage chamber 102, including within PCI 110, measured by negative pressure sensor 192. Preferably, programmable controller 186 monitors the negative pressure during a treatment at a predetermined sampling rate.

At 284, programmable controller 186 determines whether the pressure measured at 282 is outside a predetermined pressure range, e.g., above a predetermined pressure. The predetermined pressure range and/or predetermined pressure may be programmed and stored in the controller's memory. The predetermined pressure may be selected as a pressure where negative pressure is not suitable, e.g., too weak, for use in apparatus 100. In one embodiment, the predetermined pressure is −30 mmHg.

If programmable controller 186 detects that the measured pressure is above the predetermined pressure, programmable controller 186 directs pressure source 162 to expand expandable cuff 142, at 286. Advantageously, expansion of expandable cuff 142 will enhance the seal around a user's appendage to minimize PCI 110 leakage through appendage opening 108 and to help permit pressure source 162 within appendage chamber 102 to create and maintain a suitable negative pressure therein.

At 288, if programmable controller 186 detects that the measured pressure is above the predetermined pressure for a predetermined period of time, e.g. 60 seconds, apparatus 100 may send an alert to the user/physician/caregiver, at 290. Sending an alert may include directing control panel 106 to visibly and/or audibly alert the user. Sending an alert may also include shutting down power to one or more components to apparatus 100 such thermal exchange member 104, pressure source 162, and/or power source 194.

If programmable controller 186 detects that the measured pressure is not above the predetermined pressure, programmable controller continues to monitor pressure at 282 until treatment is completed.

As discussed above, the methods and apparatus of the present invention are intended to create or assist in maintaining vasodilation and enhancing the transfer to energy to an arteriovenous anastomosis vascular area in a mammal, deliver heating or cooling to a body core of the mammal using the dilated arteriovenous anastomosis vascular area pulled closer to the skin by negative pressure, and in heating mode may continue to deliver heat to the body core using the dilated arteriovenous anastomosis vascular area to a body at normothermia pre-treatment or to a body at sub-normothermia pre-treatment such that the body core reaches normothermia. Applicant believes that continuing to deliver heat to the dilated arteriovenous anastomosis area to a body at normothermia, or to a body core that has reached normothermia, causes secondary vasodilation in other arteriovenous anastomosis and peripheral vascular areas throughout the entire body to dissipate the excess heat being infused by the apparatus. The rapid delivery by the circulatory system of the blood needed to fill these newly dilated heat exchange-vascular structures increases microvascular circulation, benefitting all organs (internal and peripheral) and the associated autoimmune, neurological, lymphatic and endocrinal systems.

Applicant has discovered that the methods and apparatus of the present invention may be used to adjust viscosity of blood in a user. For example, it is expected that the methods and apparatus of the present invention may be used to deliver heating or cooling to blood flowing through the AVA at a temperature and for a duration, e.g., using thermal exchange member 104, sufficient to adjust a viscosity of blood in the human to alleviate a symptom associated with a number of autoimmune, circulatory, neurological, lymphatic, and/or endocrinal maladies, or any combinations thereof. Without wishing to be bound by such theory as to the mechanism of action, it is expected that the reduction of blood viscosity increases microvascular circulation and alleviates a symptom(s) associated with all diseases or conditions associated with systemic inflammation or hyperviscosity of the blood including, but not limited to, hypertension, occlusive arterial disease, myocardial infarction, kidney failure, hyperglycemia, preeclampsia, and dyslipidemia.

In addition, the methods and apparatus of the present invention may be used to reduce core body temperature for treatment of heart attack, stroke, heat stroke, reduction of fever including fever not resulting from an immune response.

As explained in U.S. Patent Application Publication No. 2012/0191022 to Muehlbauer, it is also expected that the methods and apparatus of the present invention may be used to treat a variety of neurological maladies that have not previously been identified as treatable by the therapeutic application of thermal energy. For example, it is expected that use of apparatus constructed in accordance with the principles of the present invention causes enhanced systemic circulation, which in turn causes redistribution of intracranial and peripheral blood flow. Without wishing to be bound by such theory as to the mechanism of action, it is expected that such redistribution may lead to varied flow patterns in the brain, e.g., in the circulation in the Circle of Willis, thereby alleviating symptoms of neurological maladies such as Parkinson's disease, migraines, Alzheimer's disease, bipolar disorder, schizophrenia, attention deficit disorder (ADD), attention deficit hyperactivity disorder (ADHD), obsessive compulsive disorder (OCD), and Autism.

It is also expected that increased circulation resulting from use of apparatus constructed in accordance with the present invention will provide several important benefits to patients suffering from poor peripheral circulation. For example, diabetic patients who maintain poor blood glucose control are known to suffer from poor peripheral blood circulation and neuropathy, often resulting in limb amputation, especially of toes. It is expected that treatments provided using the apparatus of the present invention will increase peripheral circulation in diabetic patients, thereby reducing the risk of occurrence of gangrene requiring amputation. In addition, the enhanced peripheral circulation is expected to reduce neuropathy in such patients, which further reduces the risk of injury to peripheral limbs and appendages necessitating amputation.

It is expected that use of the methods and apparatus of the present invention also may promote wound healing by stimulating the lymphatic system. In particular, delivering heat to a normothermic person (a person having approximately normal body temperature) has been observed to increase whole body circulation. While not wishing to be bound by any theory as to the mechanism of action, it is believed that such increased circulation will also stimulate the lymphatic and endocrinal systems. With respect to the lymphatic system, which controls transmission of intracellular fluids, an increase in blood circulation also is expected to produce a corresponding increase in flow in the lymph system. For a patient suffering from chronic wounds, such as diabetic ulcers, stimulation of the lymphatic system is expected to improve flow of exudate to the site of the chronic wound. Provided that steps are taken to prevent pooling of exudate at the wound site (e.g., to prevent bacterial growth), such increased exudate is expected to wash toxins from the wound bed, and more quickly deliver materials (platelets and proteins) to the wound site that facilitate wound healing.

Improved functioning of the lymph system resulting from use of the apparatus of the present invention also may be beneficial for patients suffering from edema, for example, resulting from end-stage renal disease or cirrhosis of the liver. In such patients, hypertension resulting from declining kidney function and/or reduced liver function due to cirrhosis can result in the buildup of excess interstitial fluid in the abdomen and legs. It is believed that by increasing whole body circulation in accordance with the present invention, multiple benefits may be achieved. First, increased whole body circulation is expected to result from vasodilation of peripheral heat exchange vessels, thereby allowing blood to fill those vessels and reduce hypertension. Second, the increased blood flow is expected to stimulate the lymphatic system, possibly facilitating the removal and processing of interstitial fluids and reducing edema. While not believed to be curative, use of the apparatus of the present invention with such patients on a regular basis, e.g., once or twice per day, may be palliative and improve the patient's quality of life.

While not wishing to be bound by any theory as to the mechanism of action, the present invention is believed to affect core body temperature by dilating or maintaining dilation in one or more arteriovenous anastomoses (AVAs) in the subject by applying a continuous temperature gradient that infuses heat into or extracts heat from the blood in the AVA vascular area pulled closer to the skin by negative pressure that is then circulated by the heart. Thermoregulatory feedback mechanisms are likely also implicated, by stimulating heat transfer at the core and/or head in response to increases in temperature elsewhere in the body. Whatever the mechanism of action, use of the invention to apply heat to the skin at a location on the body remote from the intended treatment site (e.g., to the extremities to thermoregulate core or cranial temperatures) produces heat transfers at the body core to therapeutic levels.

It is further believed that use of the methods of the invention will have an effect on metabolic processes in the body by affecting the activity of certain enzymes and hormones. For example, the thermoregulatory changes produced by use of the invention may influence the activity of enzymes involved in pain, such as prostaglandin-E synthesizing (PEGS) enzymes, COX enzymes (1, 2 and/or 3), and/or microsomal PEGS-1 (mPEGS), most likely by increasing enzyme kinetics slowed by abnormally low core body temperatures. In metabolic disorders such as hypothyroidism, the body temperature is lowered and enzyme function decreases, slowing metabolism and leading to weight gain and fatigue. Raising body temperature according to the invention may restore the enzymes' kinetic rate and positively affect metabolic disorders.

Patients in a pre-diabetic or diabetic state, as clinically measured from blood glucose and/or A1C levels in the subject over time, may experience increased weight loss using of the methods of the invention. Insulin dependent diabetics may find their need for insulin reduced by 60 to 70% within a relatively short period of time. Again, while not wishing to be bound by any theory as to mechanism of action, the potential impact on metabolic processes as described herein may be in play in pre-diabetic and diabetic individuals, in whom core body temperatures may become sub-normothermic over time or normothermic individuals that may benefit from increased circulation.

The biological responses produced by use of the invention have therapeutic implications for a further range of conditions. For example, migraines, chronic fatigue syndrome, and certain autoimmune disorders share symptoms with autonomic and sympathetic nervous system (SNS) hypofunction. The SNS controls blood vessel constriction, decreasing blood flow to extremities when activated. Warmed blood from the heart will first warm the SNS nerve nexus behind the heart. This SNS influence may then reverse the SNS hypofunction and in turn reverse the symptoms of the condition being treated. Therefore, in preferred embodiments, the invention may be used to treat migraines and also to reduce the incidence of pre-migraine events, such as prodromes and auras.

Thermal energy also may to be removed from the head to provide beneficial effects. In some embodiments, thermal energy is removed from the head arterial blood supply, e.g., carotid arterial blood. Those of ordinary skill in the clinical arts will be familiar with or may readily ascertain other measures for beneficial improvements in the condition of treated patients; e.g., reductions in body mass, improvements in neurological function as evidenced by motor function test results, and the like.

In addition, circulatory disorders associated with vasoconstriction in the extremities (such as carpal tunnel syndrome, trigger finger and arthritis) may be treated. Treatment of dermatological disorders associated with restricted blood flow to the skin (such as eczema) may also be effected by increasing the local flow of blood and oxygen to a treatment site. Disorders known to disrupt thermoregulatory processes such as stress, anxiety, neurodegenerative conditions such as multiple sclerosis and fibromyalgia, as well as sequalae of chemotherapy (affecting digestion) and irritable bowel syndrome (affecting bowel regularity) may also be beneficially affected by use of the invention.

The above described thermal energy treatments may be performed with or without the aid of automated data collection devices and/or processors. As such, in certain embodiments one or more sensors are employed to detect temperatures in the core body and head region of the mammal. Any convenient temperature sensing devices may be employed, where suitable devices include: thermocouples, thermistors, microwave temperature sensors, infrared cameras, and the like. The position and nature of the temperature sensing devices necessarily depends on whether it is to detect the core body or head temperature of the mammal. For detecting thoracic/abdominal core body temperature, sensor locations of interest include: the esophagus, the rectum, and in the case of microwave detection, anywhere on the surface of the body to measure the underlying temperature. For head temperature, sensor locations of interest include: the auditory canal, the oral cavity, and in the case of microwave detection, anywhere on the surface of the head to measure the underlying temperature.

The data collected from these sensor devices may be processed by a processor to at least display the data for the operator in a user friendly/readable format. The data may also be processed by a processor which causes or inhibits the thermal energy transfer events in response to the detected data or variations therein.

Examples of the practice of the invention are set forth below. These examples shall not be considered to limit the invention, whose scope is defined by the appended claims.

EXAMPLE 1

Blood Viscosity Adjustment

A beneficial improvement in reducing blood viscosity of human patients was confirmed by blood testing when undergoing a heating treatment in accordance with the present invention. Six vials of blood were drawn from a patient's left arm before treatment on the right hand, and six vials of blood were drawn from the patient's left arm following treatment. The patient underwent a first treatment using a previously known device, referred to as "Machine 1", and, at a later date, underwent a second treatment using apparatus and methods described herein in accordance with the present invention, referred to as "Machine 2".

| | Patient | | | |
|---|---|---|---|---|
| | Treatment 1/Machine 1 | | Treatment 2/Machine 2 | |
| | Pre-Treatment | Post-Treatment | Pre-Treatment | Post-Treatment |
| Systolic Viscosity | 38.5 | 36.8 | 36.7 | 32.8 |
| Diastolic Viscosity | 110.8 | 103.1 | 98.7 | 87.2 |

The test results show a 4.42% reduction in systolic viscosity and a 6.95% reduction in diastolic viscosity after the first 20 minute treatment using the previously known device. After the second 20 minute treatment, nine days later, the test results reveal an 18.41% reduction in systolic viscosity and a 21.3% reduction in diastolic viscosity using apparatus and methods in accordance with the present invention. As will be apparent to one of ordinary skill in the art, treatment using apparatus and methods in accordance with the present invention provides a dramatic blood viscosity reduction.

EXAMPLE 2

Blood Viscosity Adjustment

Figure 7A:
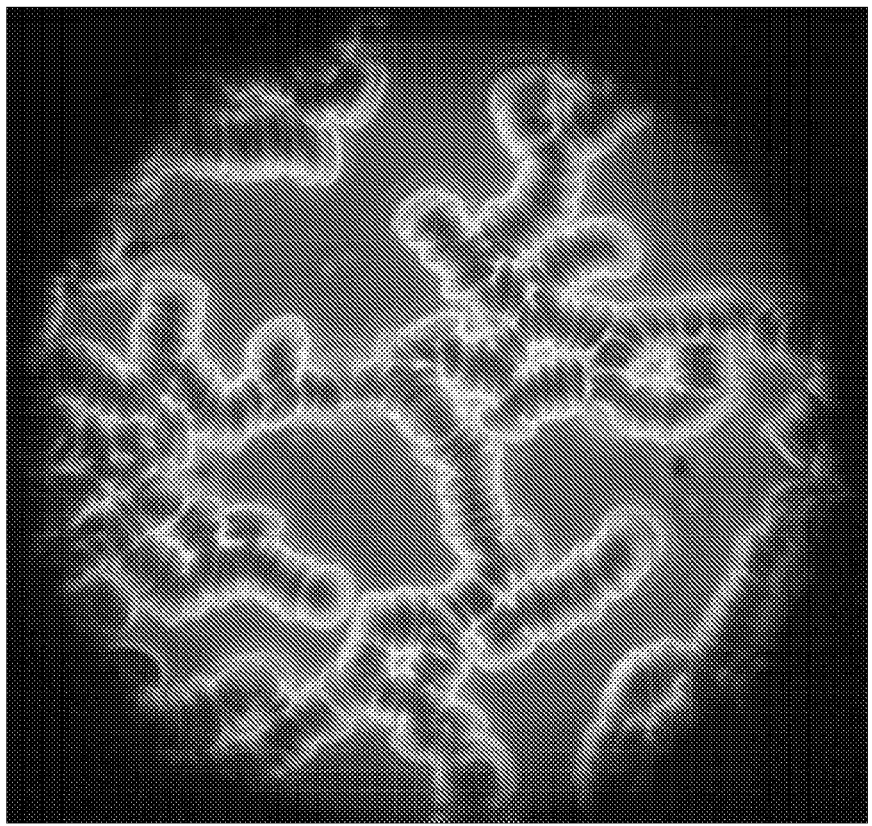
FIGS. 7A and 7B are images from a microscope of red blood cells within a blood sample from a patient treated in accordance with methods of the present invention, before and after treatment, respectively.
Figure 7B:
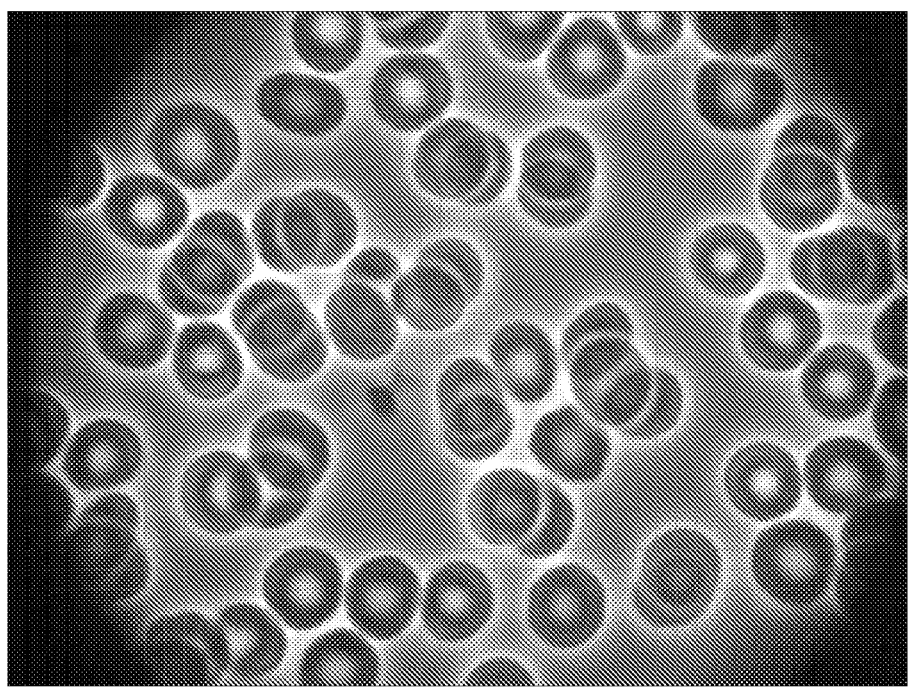

FIGS. 7A and 7B are images from a microscope of red blood cells within a blood sample taken from the hand opposite the treatment hand of a patient. Before treatment, the red blood cells were bunched together (rouleaux formation) as shown in FIG. 7A. Rouleaux affects proper oxygenation because the red blood cells do not circulate well enough to deliver oxygen where it is needed. Conditions which cause rouleaux formation include infections, inflammatory and connective tissue disorders, and cancers. It also occurs in diabetes mellitus and is one of the causative factors for microvascular occlusion in diabetic retinopathy. After a 20 minute warming treatment using methods in accordance with the present invention, the red blood cells become symptomatic of healthy blood, as shown in FIG. 7B. Without wishing to be bound by such theory as to the mechanism of action, it is expected that the healthy red blood cells are the result of a reduction in patient blood viscosity thereby rapidly increasing microvascular circulation, oxygenation and protein delivery to alleviate symptom(s) associated with all diseases or conditions associated with systemic inflammation or hyperviscosity of the blood.

EXAMPLE 3

Blood Viscosity Adjustment

Figure 8A:
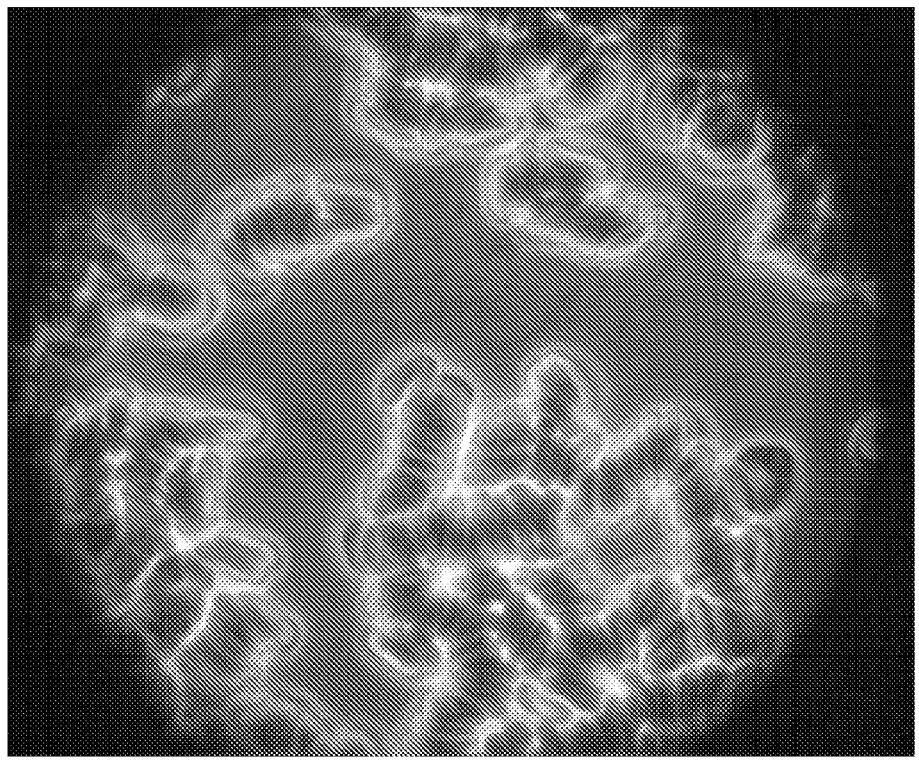
FIGS. 8A and 8B are images from a microscope of red blood cells within a blood sample from another patient treated in accordance with methods of the present invention, before and after treatment, respectively.
Figure 8B:
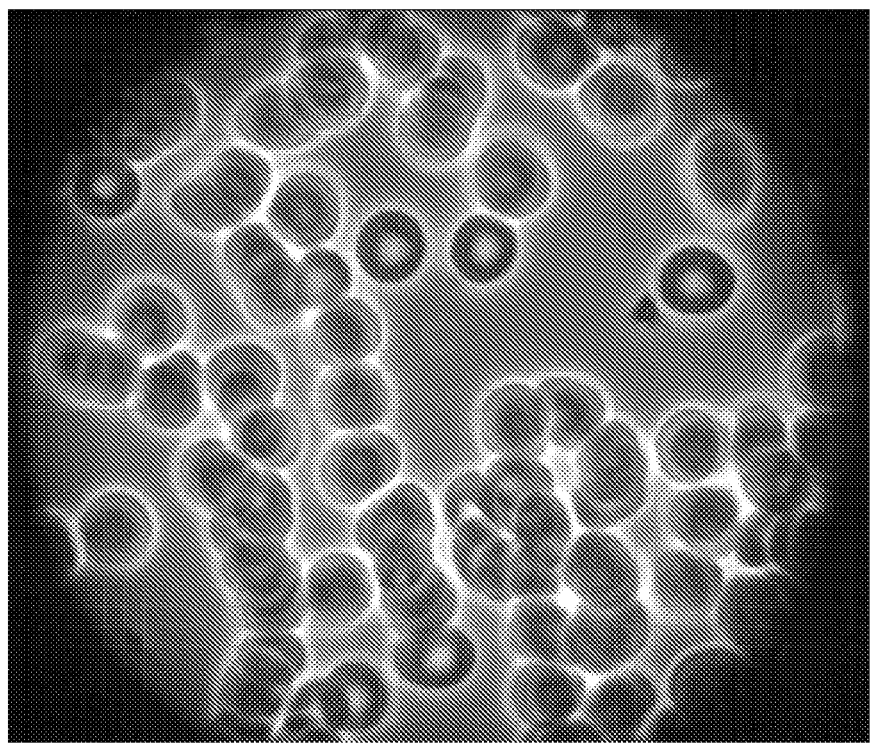

FIGS. 8A and 8B are images from a microscope of red blood cells within a blood sample taken from the hand opposite the treatment hand of another patient treated in accordance with methods of the present invention, before and after treatment, respectively. Consistent with the results described above with respect to FIGS. 7A and 7B, FIG. 8B shows that the red blood cells present healthy characteristics after a 20 minute warming treatment using apparatus and methods in accordance with the present invention, as compared to the rouleaux alignment of red blood cells pre-treatment in FIG. 8A.

EXAMPLE 4

Fibromyalgia

In an Independent Review Board controlled proof of concept study conducted by the US Department of Veterans Affairs and the University of San Diego, Calif., five patients having physician diagnosed fibromyalgia underwent one heating treatment per day for 10 minutes over 28 days, in accordance with the methods of the present invention. The reported results are in the Table below.

|  | Patient 1 | | Patient 2 | | Patient 3 | | Patient 4 | | Patient 5 | |
| --- | --- | --- | --- | --- | --- | --- | --- | --- | --- | --- |
|  | Pre | Post | Pre | Post | Pre | Post | Pre | Post | Pre | Post |
| Widespread Pain Index | 15 | 13 | 13 | 13 | 15 | 8 | 18 | 17 | 16 | 14 |
| Tender Point Count | 12 | 8 | 14 | 6 | 15 | 14 | 18 | 17 | 18 | 18 |
| Depression | Severe | Moderate | Minimal | Minimal | Minimal | Minimal | Mild | Minimal | Severe | Severe |

As may be observed from studying the Table, four patients reported improvement in Widespread Pain Index while one patient demonstrated no improvement; four patients reported a reduction in Tender Point Count with the reduction of Patient 1 and 2 being so significant that they no longer met the fibromyalgia diagnosis criteria minimum tender point count of 11, while one patient showed no improvement; and two patients reported improvement in Depression while three patients reported no improvement.

While various illustrative embodiments of the invention are described above, it will be apparent to one skilled in the art that various changes and modifications may be made therein without departing from the invention. The appended claims are intended to cover all such changes and modifications that fall within the true scope of the apparatus and methods of the present invention.

What is claimed:

1. Apparatus for treating a condition of a human, the apparatus comprising:
    an appendage chamber having an expandable cuff with an appendage opening configured to accept a human appendage containing an arteriovenous anastomosis (AVA);
    a thermal exchange member disposed within the appendage chamber, the thermal exchange member configured to selectively heat or cool blood flowing through the appendage containing the AVA, the thermal exchange member comprising a Peltier device or components for resistive heating or both;
    a disposable flexible membrane having a membrane opening configured to accept the appendage, the disposable flexible membrane configured to be at least partially disposed within the appendage chamber and to be removable from the appendage chamber;
    a pressure source disposed within the appendage chamber and comprising a single motor-driven pump, the pump coupled via an opening to the appendage chamber and coupled via a pressure line to the expandable cuff, the pump capable of applying negative pressure to the appendage chamber and applying positive pressure to the pressure line to expand the expandable cuff such that the disposable flexible membrane conforms to the expandable cuff to seal around the appendage, when the appendage within the flexible membrane is placed within the appendage chamber;
    a negative pressure sensor configured to measure a pressure within the appendage chamber; and
    a programmable controller configured to:
        monitor the pressure measured by the negative pressure sensor, and direct the pressure source to expand the expandable cuff if the measured pressure is above a predetermined pressure;
    wherein the flexible membrane comprises at least one pressure equalizing vent configured to permit a fluid to be drawn from within the flexible membrane through the at least one pressure equalizing vent as negative pressure is applied via the pressure source to create a negative pressure environment within the flexible membrane.

2. The apparatus of claim 1, wherein the appendage chamber comprises a pressure chamber insert having the expandable cuff,
    wherein the pressure chamber insert is configured to be removable from the appendage chamber.

3. The apparatus of claim 2, further comprising a sealing pad disposed within the appendage chamber, the sealing pad having a sealing pad opening configured to be disposed around the thermal exchange member,
    wherein the sealing pad is configured to be coupled to the pressure chamber insert to enhance application of negative pressure therein.

4. The apparatus of claim 1, further comprising a deformable pad disposed within the appendage chamber, the deformable pad configured to contact the appendage and the appendage chamber to urge the appendage onto the thermal exchange member.

5. The apparatus of claim 1, further comprising a load sensor coupled to the thermal exchange member, the load sensor configured to measure a force of the appendage applied to the thermal exchange member.

6. The apparatus of claim 1, wherein the programmable controller is configured to monitor application of negative pressure within the appendage chamber responsive to the pressure measured by the negative pressure sensor.

7. The apparatus of claim 1, wherein the thermal exchange member is configured to heat or cool the blood at a temperature and for a duration sufficient to adjust a viscosity of the blood.

8. The apparatus of claim 1, wherein the programmable controller is configured to control heating or cooling of the thermal exchange member responsive to user input or a preselected therapy regime.

9. The apparatus of claim 8, wherein the preselected therapy regime is selected to alleviate a symptom associated with an autoimmune, circulatory, neurological, lymphatic, thermoregulatory disorders, or endocrinal dysfunction, or any combination thereof including Parkinson's disease, diabetic neuropathy, migraine headaches, Alzheimer's disease, arthritis, fibromyalgia, Lyme disease, bipolar disorder, schizophrenia, attention deficit disorder (ADD), attention deficit hyperactivity disorder (ADHD), obsessive compulsive disorder (OCD), Autism, and hyperviscosity.

\* \* \* \* \*